United States Patent
Kadyk et al.

(10) Patent No.: US 8,481,269 B2
(45) Date of Patent: Jul. 9, 2013

(54) PIK4CA AS MODIFIER OF THE RAC PATHWAY AND METHODS OF USE

(75) Inventors: Lisa C. Kadyk, San Francisco, CA (US); George Ross Francis, Pacifica, CA (US); Lynn Margaret Bjerke, Sutton (GB); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 756 days.

(21) Appl. No.: 11/575,233

(22) PCT Filed: Sep. 15, 2005

(86) PCT No.: PCT/US2005/032838
§ 371 (c)(1),
(2), (4) Date: Mar. 7, 2008

(87) PCT Pub. No.: WO2006/033942
PCT Pub. Date: Mar. 30, 2006

(65) Prior Publication Data
US 2008/0263684 A1  Oct. 23, 2008

Related U.S. Application Data

(60) Provisional application No. 60/611,127, filed on Sep. 17, 2004.

(51) Int. Cl.
*C12Q 1/34* (2006.01)

(52) U.S. Cl.
USPC ....... 435/6.18; 435/6.11; 435/6.13; 435/6.14; 435/7.23; 424/9.2

(58) Field of Classification Search
None
See application file for complete search history.

(56) References Cited

U.S. PATENT DOCUMENTS

2002/0192695 A1* 12/2002 Friedman et al. ............... 435/6
2004/0219616 A1  11/2004 Seery et al.

FOREIGN PATENT DOCUMENTS

WO  WO 2004/048540 A2  6/2004

OTHER PUBLICATIONS

Saito et al. Polymorphism screening of PIK4CA: possible candidate gene for chromosome 22q11-linked psychiatric disorders, Am J Med Genet B Neuropsychiatr Genet. 116B (1):77-83, 2003.*
Saito et al., Polymorphism screening of PIK4CA: possible candidate gene for chromosome 22q11-linked psychiatric disorders, Am J Med Genet B Neuropsychiatr Genet. 116B(1):77-83, 2003.*
Andjelkovic et al., Activation and phosphorylation of a pleckstrin homology domain containing protein kinase (RAC-PK/PKB) promoted by serum and protein phosphatase inhibitors, Proc Natl Acad Sci U S A. 93(12):5699-704, 1996.*
Huang et al., Parallel activation of phosphatidylinositol 4-kinase and phospholipase C by the extracellular calcium-sensing receptor, J Biol. Chem. 277(23):20293-300, 2002.*
Matsuzaki et al., Isolation of the active form of RAC-protein kinase (PKB/Akt) from transfected COS-7 cells treated with heat shock stress and effects of phosphatidylinositol 3,4,5-trisphosphate and phosphatidylinositol 4,5-bisphosphate on its enzyme activity, FEBS Lett. 396(2-3):305-8, 1996.*
Harris, A.J. et al.: "Comparison of basal gene profiles and effects of hepatocarcinogens on gene expression in cultured primary human hepatocytes and HepG2 cells," Mutation Research, Jan. 2004, vol. 549, No. 1, pp. 79-99.
Nakagawa, N. et al.: "Cloning, Expression and Localization of 230-kDa Phosphatidylinositol 4-Kinase," The Journal of Biological Chemistry, May 17, 1996, vol. 271, No. 20, pp. 12088-12094.
Sendger, D. L. et al.: "Suppression of Rac Activity Induces Apoptosis of Human glioma Cells but not Normal Human Astrocytes," Cancer Research, Apr. 1, 2002, vol. 62, pp. 2131-2140.
Ishikawa S. et al.: "Identification of genes related to invasion and metastasis in pancreatic cancer by cDNA representational difference analysis," Journal of Experimental & Clinical Cancer Reearch, vol. 22, No. 2 Jun. 2003, pp. 299-306.
Singhal R. L. et al.: "Coordinated increase in activities of the signal transduction enzymes PI kinase and PIP kinase in human cancer cells," Life Sciences, Pergamon Press, Oxford, GB, vol. 55, No. 19, Jan. 1, 1994, pp. 1487-1492.
Rizzo, Maria Teresa et al.: "1-Phosphatidylinositol 4-kinase: An enzyme linked with proliferation and malignancy," Cancer Research, vol. 54, No. 10, 1994, pp. 2611-2614.
GenBank Reference No. 4505806 (NM_002650.1) entitled: "*Homo sapiens* phosphatidylinositol 4-kinase, catalytic, alpha polypeptide (PIK4CA), transcript variant 1, mRNA." dated Aug. 23, 2004.
GenBank Reference No. 17105399 (NM_058004.2) entitled: "*Homo sapiens* phosphatidylinositol 4-kinase, catalytic, alpha (PI4KA), transcript variant 2, mRNA," dated Aug. 23, 2004.
GenBank Reference No. 17390265 (BC018120.1) entitled: "*Homo sapiens* phosphatidylinositol 4-kinase, catalytic, alpha, mRNA (cDNA clone Image:3912560), partial cds," dated Jul. 2, 2003.
GenBank Reference No. 32197215 (BC053654.1) entitled: "*Homo sapiens* phosphatidylinositol 4-kinase, catalytic, alpha, mRNA (cDNA clone Image:5757080), partial cds," Jun. 25, 2003.
GenBank Reference No. 21755146 (AK095811.1) entitled: "*Homo sapiens* cDNA FLJ38492 fis, clone EHRT2000325, highly similar to Phosphatidylinositol 4-kinase alpha (EC 2.7.1.67)," dated Jan. 30, 2004.
GenBank Reference No. 34530550 (AK124692.1) entitled: "*Homo sapiens* cDNA FLJ42702 fis, clone RAMY3005091, highly similar to Phosphatidylinositol 4-kinase alpha (EC 2.7.1.67)," dated Sep. 8, 2003.
GenBank Reference No. 17105400 (NP_477352.1) entitled: "Phosphatidylinositol 4-kinase, catalytic, alpha polypeptide isoform 2 [*Homo sapiens*]," dated Aug. 23, 2004.

* cited by examiner

*Primary Examiner* — Jon P Weber
*Assistant Examiner* — Chunyuan Luo
(74) *Attorney, Agent, or Firm* — McDonnell Boehnen Hulbert & Berghoff LLP

(57) ABSTRACT

Human PIK4CA genes are identified as modulators of the RAC pathway, and thus are therapeutic targets for disorders associated with defective RAC function. Methods for identifying modulators of RAC, comprising screening for agents that modulate the activity of PIK4CA are provided.

8 Claims, No Drawings

SEQUENCE LISTING

<160> NUMBER OF SEQ ID NOS: 8

<210> SEQ ID NO 1
<211> LENGTH: 3034
<212> TYPE: DNA
<213> ORGANISM: Homo sapiens

```
<400> SEQUENCE: 1
tggtttctaa atcttattca gtgagcacgt gttcctttt ttaattagag aaaacttgac      60
agtagcccct ttttgtgttt cacagaggag ctaacattcc ttctgtacct gtagttcatg     120
cgggagatgg caggggcctg gcacatgacg gtggagcaga aatttggcct gttttctgct    180
gagataaagg aagcagaccc cctggctgcc tcggaagcaa gtcaacccaa accctgtccc    240
cccgaagtga cccccccacta catctggatc gacttcctgg tgcagcggtt tgagatcgcc    300
aagtactgca gctctgacca agtggagatc ttctccagcc tgctgcagcg ctccatgtcc    360
ctgaacatcg gcggggccaa ggggagcatg aaccggcacg tggcggccat cgggccccgc    420
ttcaagctgc tgaccctggg gctgtccctc ctgcatgccg atgtggttcc aaatgcaacc    480
atccgcaatg tgcttcgcga agatctctac tccactgcct ttgactactt cagctgtccc    540
ccaaagttcc ctactcaagg agagaagcgg ctgcgtgaag acataagcat catgattaaa    600
ttttggaccg ccatgttctc agataagaag tacctgaccg ccagccagct tgttccccca    660
gataatcagg acacccggag caacctggac ataactgtcg gctctcggca acaagccacc    720
caaggctgga tcaacacata cccctgtcc agcggcatgt ccaccatctc caagaaatca    780
ggcatgtcta agaaaaccaa ccggggctcc cagctgcaca atactacat gaagcgcagg    840 acgctgctgc tgtccctgct ggccactgag atcgagcgtc tcatcacatg gtacaacccg    900
ctgtcagccc cggaactgga actagaccag gccggagaga cagcgtggc caactggaga    960 tctaagtaca tcagcctgag tgagaagcag tggaaggaca cgtgaacct cgcctggagc   1020 atctctccct acctagccgt gcagctgcct gccaggttta gaacacaga agccattggg   1080 aacgaagtga cccgtctcgt tcggttggac ccggagccg ttagtgatgt gcctgaagca    1140
atcaagttcc tggtcacctg gcacaccatc gacgccgatg ctccagagct cagccatgtg   1200
ctgtgctggg cgcccacgga cccacccaca ggcctctcct acttctccag catgtacccg   1260 ccgcacccc tcacggcgca gtacggggtg aaagtcctgc ggtccttccc tccggacgcc   1320
atcctcttct acatccccca gattgtgcag gccctcaggt acgacaagat gggctatgtg   1380
cgggagtata ttctgtgggc agcgtctaaa tcccagcttc tggcacacca gttcatctgg   1440
aacatgaaga ctaacatttta tctagatgaa gagggccacc agaaagaccc tgacatcggc   1500
gacctcctgg atcagttggt agaggagatc acaggctcct tgtccggccc agcgaaggac   1560
ttttaccagc gggagtttga tttctttaac aagatcacca cgtgtcggc tatcatcaag   1620 ccctacccta aaggcgacga gagaaagaag gcttgtctgt cggccctgtc tgaagtgaag   1680
gtgcagccgg gctgctacct gcccagcaac cctgaggcca ttgtgctgga catcgactac   1740
aagtctggga ccccgatgca gagtgctgca aaagcccat atctggccaa gttcaaggtg   1800
aagcgatgtg gagttagtga acttgaaaaa gaaggtctgc ggtgccgctc agactccgag   1860
gatgagtgca gcacgcagga ggccgacggc cagaagatct cctggcaggc agccatcttc   1920
aaggtgggag acgactgccg gcaggacatg ctggccctgc agatcatcga cctcttcaag   1980
aacatcttcc agctggtcgg cctggacctc tttgttttc cctaccgcgt ggtggccact   2040
gcccctgggt gcggggtgat cgagtgcatc cccgactgca cctcccggga ccagctgggc   2100
cgccagacag acttcggcat gtacgactac ttcacgcgcc agtacgggga tgagtccact   2160
ctggccttcc agcaggcccg ctacaacttc atccgaagca tggccgccta cagcctcctg   2220
ctgttcctgc tgcagatcaa ggacagacac aacggcaaca ttatgctgga caagaagggt   2280
catatcatcc acatcgactt tgggttcatg tttgaaagct cgccgggcgg caatctcggc   2340
```

```
tgggaacccg acatcaagct gacggatgag atggtgatga tcatgggggg caagatggag   2400
gccacaccct tcaagtggtt catggagatg tgtgtccgag gctacctggc tgtgcggccc   2460
tacatggacg cggtcgtctc cctggtcact ctcatgttgg acagggcct gccctgtttt    2520 cgcggccaga caatcaagct cttgaagcac aggtttagcc ccaacatgac tgagcgcgag   2580
gctgcaaatt tcatcatgaa ggtcatccag agctgcttcc tcagcaacag gagccggacc   2640
tacgacatga tccagtacta tcagaatgac atcccctact gaggagggga ccttcgaggg   2700
cctctgcccc atgtgccctc aaagctgtcc cacaatcatg gagccctgcg acctccctgc   2760
cctgccgcca catgcagtgg aggagaggcc tgtggcccaa agaacctggt agcgcctcct   2820
ggggcagcac gtgggtggcg cagccttggt aacgccatgg actgcagcga caatcaatgg   2880
atggtgctgt ctatgcacag gtgtgagtcc tctgttttgca ctggacatat ccctacctg   2940 tcttatttca taggtacatg aagtattgtg tataaaaaaa gagataagat ttaaccaaca   3000
tcaacaaaat aaaaacccaa aatagtaaaa accc                              3034

<210> SEQ ID NO 2
<211> LENGTH: 6502
<212> TYPE: DNA
<213> ORGANISM: Homo sapiens

<400> SEQUENCE: 2
atgtgcccag tagattttca tgggatcttc cagttagatg aaagacggag agatgcagtg     60
attgcattgg cattttctct gattgaatct gatcttcagc acaaagattg tgtggttcct    120
taccttcttc gacttctcaa aggtcttcca aaagtgtatt gggtagaaga agcacagct     180 cggaaaggca gaggtgccct cccggttgca gagagcttca gcttctgctt ggtaactctg    240
ctgtctgatg tggcctatag ggatccttca cttagggatg agattttaga ggtgcttttg    300
caggttttgc atgtcctctt ggggatgtgc caggccttgg agattcaaga caaagaatac    360 cttttgcaagt atgctatccc atgcctgata ggaatctcgc gagcatttgg gcgttacagc    420
aacatggaag agtctctcct ctcaaagctc tttcccaaaa tccctcctca ttccctccgt    480
gtcctggaag agcttgaagg tgttcgaagg cgttccttta atgacttccg ctccatcctc    540
cccagcaatc tgctgactgt ctgtcaggag ggtaccctga gaggaaaaac cagcagtgtg    600
tccagcatct ctcaggtcag ccctgaacgc ggcatgcccc tcccagttc ccctggagga     660 tctgcctttc actactttga agcctcctgt tgcccgatg ggactgccct agagcctgag     720
tactactttt caaccatcag ctccagcttc tcagtctctc cccttttcaa cggtgtcaca    780
tataaggagt ttaacattcc attggaaatg cttcgggaac tcttaaacct ggtgaagaag    840
atcgttgagg aggctgttct caaatctttg gatgccattg tagccagtgt gatggaggcc    900
aaccccagtg ctgatcttta ctacacttcc ttcagtgacc ctctctacct gaccatgttc    960
aagatgctgc gtgacactct gtactacatg aaggacctcc cgacctcttt tgtgaaggag   1020
atccatgatt ttgtgctgga gcagttcaac acgagccagg gggagctcca aaagattcta   1080
catgacgcag accggatcca caatgagctg agccccctca actgcgctg tcaggcgagt   1140 gctgcctgtg tggacctcat ggtgtgggct gtgaaggacg agcagggtgc agaaaaacctt  1200 tgcatcaagc tatctgagaa gctgcagtcc aagacgtcca gcaaagtcat tattgctcac   1260
ttgcccctgc tgatctgctg tctgcagggt ttgggccgcc tgtgcgagag gttcccggtg   1320
gtggtgcact ctgtgacacc gtccttgcga gacttcctgg tcatcccgtc ccagttctgt   1380
gtgaagctct acaagtacca cagtcagtac cacacagttg ctggcaatga tataaaaatc   1440
```

```
agtgtgacca atgagcattc cgagtcaacc ctgaacgtca tgtcgggtaa gaagagccag    1500
ccctccatgt acgagcagct ccgagacatc gctattgaca acatctgcag gtgcctgaag    1560
gctggattga cggtggaccc agtgattgtg gaggcgttct tggccagcct gtccaaccgg    1620
ctctacatct ctcaggagag cgacaaggac gctcacttga ttcccgacca cacaatccga    1680
gccttgggac acattgcggt ggccttgagg gacaccccga aggtcatgga gcccattctg    1740
cagatcctac agcagaaatt tgccagcca ccctcccccc tcgatgtgct gattattgac    1800
cagctgggct gcctggttat caccggaaat caatacatct atcaggaagt gtggaacctc    1860
ttccagcaga tcagtgtgaa ggccagctcc gttgtatact cagccaccaa agattacaag    1920
gaccacggct ataggcattg ctccctggca gtgattaatg ccctggccaa catcgcggcc    1980
aacatccaag acgagcacct ggtggatgag ctgctcatga acctgttgga gttgtttgtg    2040
cagctggggc tggaggggaa gcgagccagc gagagggcaa gcgagaaggg ccctgcccta    2100
aaggcttcta gcagtgcagg gaacttggga gtactcattc ctgtaatagc tgtgctcacc    2160
cgacgactgc cacccatcaa agaagctaag cctcggttac agaagctctt ccgagacttc    2220
tggctgtatt ccgttctgat gggattcgct gtggagggct caggactctg gcagaagaa    2280 tggtacgagg gggtctgtga aatagccact aagtcccct tgctcaccttt tcccagcaag    2340 gagccactgc ggtccgtcct ccagtataac tcagccatga agaatgacac ggtcaccccc    2400
gctgagctga gtgagctccg cagcactatc atcaacctgc tggaccccc tcccgaggtg    2460 tccgcactca tcaacaagct ggacttcgcc atgtccacct acctcctctc tgtgtaccgg    2520
ctggagtaca tgagggtact gcgttcaaca gatcctgatc gcttccaggt aatgttctgc    2580
tactttgagg ataaagctat tcagaaagac aaatctggga tgatgcagtg tgtgattgca    2640
gtcgcggaca aagtattcga tgccttcctg aacatgatgg cggataaagc caagaccaag    2700
gagaacgagg aggagctgga gcggcacgct cagttcctgt tggtgaactt caaccacatc    2760
cacaagagga taaggagggt ggcagacaag tatctatctg gtctggtgga taagtttccc    2820
cacttgctct ggagcgggac tgtgctgaag accatgctgg acatcctgca gcccctgtca    2880
ctgtcactga gcgctgatat tcacaaggat cagccttact atgacatccc cgacgccccc    2940
taccggatca cggttcctga cacgtacgaa gcccgtgaga gcattgtgaa ggacttcgct    3000
gcacgctgtg gatgatcct ccaggaggcc atgaagtggg cacctaccgt caccaagtcc    3060
cacctgcagg aatatctgaa caaacatcag aactgggtat cgggactgtc ccagcacaca    3120
gggctggcca tggccactga gagcatcctt cactttgctg gctacaacaa gcagaacaca    3180
actcttgggg caactcagct gagcgagcgc ccggcctgtg tgaagaaaga ctactccaac    3240
ttcatggcat ccctgaatct gcgcaaccgc tacgcgggcg aggtgtatgg aatgattcgg    3300
ttctcaggca ccacaggcca gatgtctgac ctgaacaaaa tgatggtcca ggatctacat    3360
tcagctttag accgcagtca tcctcagcac tacacgcagg ccatgttcaa gctgaccgca    3420
atgctcatta gcagtaaaga ttgtgacccg cagctccttc atcatctgtg ctggggtccc    3480
ctccggatgt tcaatgagca tggcatggag acggccctgg cctgctggga gtggctgctg    3540
gctggcaagg atggagtgga agtgccgttc atgcgggaga tggcaggggc ctggcacatg    3600
acggtggagc agaaatttgg cctgttttct gctgagataa aggaagcaga ccccctggct    3660
gcctcggaag caagtcaacc caaaccctgt cccccgaag tgaccccca ctacatctgg    3720 atcgacttcc tggtgcagcg gtttgagatc gccaagtact gcagctctga ccaagtggag    3780
atcttctcca gcctgctgca gcgctccatg tccctgaaca tcggcggggc caaggggagc    3840
```

```
atgaaccggc acgtggcggc catcgggccc cgcttcaagc tgctgaccct ggggctgtcc      3900
ctcctgcatg ccgatgtggt tccaaatgca accatccgca atgtgcttcg cgagaagatc      3960
tactccactg cctttgacta cttcagctgt cccccaaagt ccctactca aggagagaag       4020 cggctgcgtg aagacataag catcatgatt aaattttgga ccgccatgtt ctcagataag      4080
aagtacctga ccgccagcca gcttgttccc cagataatc aggacacccg gagcaacctg       4140
gacataactg tcggctctcg gcaacaagcc acccaaggct ggatcaacac ataccccctg      4200
tccagcggca tgtccaccat ctccaagaaa tcaggcatgt ctaagaaaac caaccggggc      4260
tcccagctgc acaaatacta catgaagcgc aggacgctgc tgctgtccct gctggccact      4320
gagatcgagc gtctcatcac atggtacaac ccgctgtcag ccccggaact ggaactagac      4380
caggccggag agaacagcgt ggccaactgg agatctaagt acatcagcct gagtgagaag      4440
cagtggaagg acaacgtgaa cctcgcctgg agcatctctc cctacctagc cgtgcagctg      4500
cctgccaggt ttaagaacac agaagccatt gggaacgaag tgacccgtct cgttcggttg      4560
gacccgggag ccgttagtga tgtgcctgaa gcaatcaagt tcctggtcac ctggcacacc      4620
atcgacgccg atgctccaga gctcagccat gtgctgtgct gggcgcccac ggacccaccc      4680
acaggcctct cctacttctc cagcatgtac ccgccgcacc ctctcacggc gcagtacggg      4740
gtgaaagtcc tgcggtcctt ccctccggac gccatcctct tctacatccc ccagattgtg      4800
caggccctca ggtacgacaa gatgggctat gtgcgggagt atattctgtg ggcagcgtct      4860
aaatcccagc ttctggcaca ccagttcatc tggaacatga agactaacat ttatctagat      4920
gaagagggcc accagaaaga ccctgacatc ggcgacctcc tggatcagtt ggtagaggag      4980
atcacaggct cctgtccgg cccagcgaag gacttttacc agcgggagtt tgatttcttt       5040
aacaagatca ccaacgtgtc ggctatcatc aagccctacc ctaaaggcga cgagagaaag      5100
aaggcttgtc tgtcggccct gtctgaagtg aaggtgcagc cggggctgcta cctgcccagc      5160 aaccctgagg ccattgtgct ggacatcgac tacaagtctg ggaccccgat gcagagtgct      5220
gcaaaagccc catatctggc caagttcaag gtgaagcgat gtggagttag tgaacttgaa      5280
aaagaaggtc tgcggtgccg ctcagactcc gaggatgagt gcagcacgca ggaggccgac      5340
ggccagaaga tctcctggca ggcagccatc ttcaaggtgg agacgactg ccggcaggac       5400 atgctggccc tgcagatcat cgacctcttc aagaacatct tccagctggt cggcctggac      5460
ctctttgttt ttccctaccg cgtggtggcc actgcccctg ggtgcggggt gatcgagtgc      5520
atccccgact gcacctcccg ggaccagctg gccgccaga cagacttcgg catgtacgac       5580
tacttcacac gccagtacgg ggatgagtcc accctggcct tccagcaggc ccgctacaac      5640
ttcatccgaa gcatggccgc ctacagcctc ctgctgttcc tgctgcagat caaggacaga      5700
cacaacggca acattatgct ggacaagaag ggccatatca tccacatcga ctttggcttc      5760
atgtttgaaa gctcgccggg cggcaatctc ggctgggaac ccgacatcaa gctgacggat      5820
gagatggtga tgatcatggg gggcaagatg gaggccacac ccttcaagtg gttcatggag      5880
atgtgtgtcc gaggctacct ggctgtgcgg ccctacatgg acgcggtcgt ctccctggtc      5940
actctcatgt tggacacggg cctgccctgt ttcgcggcc agacaatcaa gctcttgaag       6000
cacaggttta gccccaacat gactgagcgc gaggctgcaa atttcatcat gaaggtcatc      6060
cagagctgct tcctcagcaa caggagccgg acctacgaca tgatccagta ctatcagaat      6120
gacatcccct actgaggagg ggaccttcga gggcctctgc cccatgtgcc ctcaaagctg      6180
tcccacaatc atggagccct gcgacctccc tgccctgccg ccacatgcag tggaggagag      6240
```

| | | |
|---|---|---|
| gcctgtggcc caaagaacct ggtagcgcct cctggggcag cacgtgggtg gcgcagcctt | | 6300 |
| ggtaacgcca tggactgcag cgacaatcaa tggatggtgc tgtctatgca caggtgtgag | | 6360 |
| tcctctgttt gcactggaca tattccctac ctgtcttatt tcataggtac atgaagtatt | | 6420 |
| gtgtataaaa aaagagataa gatttaacca acatcaacaa aataaaaacc caaaatagta | | 6480 |
| aaaacccaaa aaaaaaaaaa aa | | 6502 |

<210> SEQ ID NO 3
<211> LENGTH: 3072
<212> TYPE: DNA
<213> ORGANISM: Homo sapiens

<400> SEQUENCE: 3

| | | |
|---|---|---|
| gctcattagc agtaaagatt gtgacccgca gctccttcat catctgtgct ggggtcccct | | 60 |
| ccggatgttc aatgagcatg gcatggagac ggccctggcc tgctgggagt ggctgctggc | | 120 |
| tggcaaggat ggagtggaag tgccgttcat gcgggagatg gcaggggcct ggcacatgac | | 180 |
| ggtggagcag aaatttggcc tgttttctgc tgagataaag gaagcagacc ccctggctgc | | 240 |
| ctcggaagca agtcaaccca aaccctgtcc ccccgaagtg acccccccact acatctggat | | 300 |
| cgacttcctg gtgcagcggt ttgagatcgc caagtactgc agctctgacc aagtggagat | | 360 |
| cttctccagc ctgctgcagc gctccatgtc cctgaacatc ggcggggcca aggggagcat | | 420 |
| gaaccggcac gtggcggcca tcgggccccg cttcaagctg ctgaccctgg ggctgtccct | | 480 |
| cctgcatgcc gatgtggttc caaatgcaac catccgcaat gtgcttcgcg agaagatcta | | 540 |
| ctccactgcc tttgactact tcagctgtcc cccaaagttc cctactcaag gagagaagcg | | 600 |
| gctgcgtgaa gacataagca tcatgattaa atttggacc gccatgttct cagataagaa | | 660 |
| gtacctgacc gccagccagc ttgttccccc agataatcag gacacccgga gcaacctgga | | 720 |
| cataactgtc ggctctcggc aacaagccac ccaaggctgg atcaacacat ccccctgtc | | 780 |
| cagcggcatg tccaccatct ccaagaaatc aggcatgtct aagaaaacca ccggggctc | | 840 |
| ccagctgcac aaatactaca tgaagcgcag gacgctgctg ctgtccctgc tggccactga | | 900 |
| gatcgagcgt ctcatcacat ggtacaaccc gctgtcagcc ccggaactgg aactagacca | | 960 |
| ggccggagag aacagcgtgg ccaactggag atctaagtac atcagcctga gtgagaagca | | 1020 |
| gtggaaggac aacgtgaacc tcgcctggag catctctccc tacctagccg tgcagctgcc | | 1080 |
| tgccaggttt aagaacacag aagccattgg gaacgaagtg accgtctcg ttcggttgga | | 1140 |
| cccgggagcc gttagtgatg tgcctgaagc aatcaagttc ctggtcacct ggcacaccat | | 1200 |
| cgacgccgat gctccagagc tcagccatgt gctgtgctgg gcgccacgg acccaccac | | 1260 |
| aggcctctcc tacttctcca gcatgtaccc gccgcaccct ctcacggcgc agtacggggt | | 1320 |
| gaaagtcctg cggtccttcc ctccggacgc catcctcttc tacatccccc agattgtgca | | 1380 |
| ggcccctcagg tacgacaaga tgggctatgt gcgggagtat attctgtggg cagcgtctaa | | 1440 |
| atcccagctt ctggcacacc agttcatctg gaacatgaag actaacattt atctagatga | | 1500 |
| agagggccac cagaaagacc ctgacatcgg cgacctcctg gatcagttgg tagaggagat | | 1560 |
| cacaggctcc ttgtccggcc cagcgaagga cttttaccag cgggagtttg atttctttaa | | 1620 |
| caagatcacc aacgtgtcgg ctatcatcaa gcccctaccct aaaggcgacg agagaaagaa | | 1680 |
| ggcttgtctg tcggccctgt ctgaagtgaa ggtgcagccg ggctgctacc tgcccagcaa | | 1740 |
| ccctgaggcc attgtgctgg acatcgacta caagtctggg accccgatgc agagtgctgc | | 1800 |
| aaaagccccca tatctggcca agttcaaggt gaagcgatgt ggagttagtg aacttgaaaa | | 1860 |

| | |
|---|---|
| agaaggtctg cggtgccgct cagactccga ggatgagtgc agcacgcagg aggccgacgg | 1920 |
| ccagaagatc tcctggcagg cagccatctt caaggtggga gacgactgcc ggcaggacat | 1980 |
| gctggccctg cagatcatcg acctcttcaa gaacatcttc cagctggtcg gcctggacct | 2040 |
| ctttgttttt ccctaccgcg tggtggccac tgcccctggg tgcggggtga tcgagtgcat | 2100 |
| ccccgactgc acctcccggg accagctggg ccgccagaca gacttcggca tgtacgacta | 2160 |
| cttcacacgc cagtacgggg atgagtccac tctggccttc cagcaggccc gctacaactt | 2220 |
| catccgaagc atggccgcct acagcctcct gctgttcctg ctgcagatca aggacagaca | 2280 |
| caacggcaac attatgctgg acaagaaggg tcatatcatc cacatcgact ttggcttcat | 2340 |
| gtttgaaagc tcgccgggcg gcaatctcgg ctgggaaccc gacatcaagc tgacggatga | 2400 |
| gatggtgatg atcatggggg gcaagatgga ggccacaccc ttcaagtggt tcatggagat | 2460 |
| gtgtgtccga ggctacctgg ctgtgcggcc ctacatggac gcggtcgtct ccctggtcac | 2520 |
| tctcatgttg gacacgggcc tgccctgttt tcgcggccag acaatcaagc tcttgaagca | 2580 |
| caggtttagc cccaacatga ctgagcgcga ggctgcaaat ttcatcatga aggtcatcca | 2640 |
| gagctgcttc ctcagcaaca ggagccggac ctacgacatg atccagtact atcagaatga | 2700 |
| catcccctac tgaggagggg accttcgagg gcctctgccc catgtgccct caaagctgtc | 2760 |
| ccacaatcat ggagccctgc gacctccctg ccctgccgcc acatgcagtg aggagaggc | 2820 |
| ctgtggccca agaacctgg tagcgcctcc tggggcagca cgtgggtggc gcagccttgg | 2880 |
| taacgccatg gactgcagcg acaatcaatg gatggtgctg tctatgcaca ggtgtgagtc | 2940 |
| ctctgtttgc actggacata ttccctacct gtcttatttc ataggtacat gaagtattgt | 3000 |
| gtataaaaaa agagataaga tttaaccaac atcaacaaaa taaaaaccca aaatagtaaa | 3060 |
| aaaaaaaaaa aa | 3072 |

```
<210> SEQ ID NO 4
<211> LENGTH: 3100
<212> TYPE: DNA
<213> ORGANISM: Homo sapiens

<400> SEQUENCE: 4
```

| | |
|---|---|
| cccgcagctc cttcatcatc tgtgctgggg tcccctccgg atgttcaatg agcatggcat | 60 |
| ggagacggcc ctggcctgct gggagtggct gctggctggc aaggatggag tggaagtgcc | 120 |
| gttcatgcgg gagatggcag gggcctggca catgacggtg gagcagaaat ttggcctgtt | 180 |
| ttctgctgag ataaaggaag cagaccccct ggctgcctcg gaagcaagtc aacccaaacc | 240 |
| ctgtccccca gaagtgaccc ccactacat ctggatcgac ttcctggtgc agcggtttga | 300 |
| gatcgccaag tactgcagct ctgaccaagt ggagatcttc tccagcctgc tgcagcgctc | 360 |
| catgtccctg aacatcggcg gggccaaggg gagcatgaac cggcacgtgg cggccatcgg | 420 |
| gccccgcttc aagctgctga ccctggggct gtccctcctg catgccgatg tggttccaaa | 480 |
| tgcaaccatc cgcaatgtgc ttcgcgagaa gatctactcc actgcctttg actacttcag | 540 |
| ctgtccccca aagttcccta ctcaaggaga gaagcggctg cgtgaagaca taagcatcat | 600 |
| gattaaattt tggaccgcca tgttctcaga taagaagtac ctgaccgcca gccagcttgt | 660 |
| tcccccagat aatcaggaca cccggagcaa cctggacata actgtcggct ctcggcaaca | 720 |
| agccacccaa ggctggatca acacataccc cctgtccagc ggcatgtcca ccatctccaa | 780 |
| gaaatcagga atgtctaaga aaaccaaccg gggctcccag ctgcacaaat actacatgaa | 840 |
| gcgcaggacg ctgctgctgt ccctgctggc cactgagatc gagcgtctca tcacatggta | 900 |

```
caacccgctg tcagcccggg aactggaact agaccaggcc ggagagaaca gcgtggccaa    960
ctggagatct aagtacatca gcctgagtga aagcagtgg aaggacaacg tgaacctcgc    1020
ctggagcatc tctccctacc tagccgtgca gctgcctgcc aggtttaaga acacagaagc    1080
cattgggaac gaagtgaccc gtctcgttcg gttggacccg ggagccgtta gtgatgtgcc    1140
tgaagcaatc aagttcctgg tcacctggca caccatcgac gccgatgctc agagctcag    1200
ccatgtgctg tgctgggcgc ccacggaccc acccacaggc ctctcctact ctccagcat    1260
gtacccgccg caccctctca cggcgcagta cggggtgaaa gtcctgcggt ccttccctcc    1320
ggacgccatc ctcttctaca tcccccagat tgtgcaggcc ctcaggtacg acaagatggg    1380
ctatgtgcgg gagtatattc tgtgggcagc gtctaaatcc cagcttctgg cacaccagtt    1440
catctggaac atgaagacta acatttatct agatgaagag ggccaccaga aagaccctga    1500
catcggcgac ctcctggatc agttggtaga ggagatcaca ggctccttgt ccggcccagc    1560
gaaggacttt taccagcggg agtttgattt ctttaacaag atcaccaacg tgtcggctat    1620
catcaagccc taccctaaag gcgacgagag aaagaaggct tgtctgtcgg ccctgtctga    1680
agtgaaggtg cagccgggct gctacctgcc cagcaaccct gaggccattg tgctggacat    1740
cgactacaag tctgggaccc cgatgcagag tgctgcaaaa gccccatatc tggccaagtt    1800
caaggtgaag cgatgtggag ttagtgaact tgaaaaagaa ggtctgcggt gccgctcaga    1860
ctccgaggat gagtgcagca cgcaggaggc cgacggccag aagatctcct ggcaggcagc    1920
catcttcaag gtgggagacg actgccggca ggacatgctg gccctgcaga tcatcgacct    1980
cttcaagaac atcttccagc tggtcggcct ggacctcttt gtttttccct accgcgtggt    2040
ggccactgcc cctgggtgcg gggtgatcga gtgcatcccc gactgcacct cccgggacca    2100
gctgggccgc cagacagact tcggcatgta cgactacttc acacgccagt acggggatga    2160
gtccactctg gccttccagc aggcccgcta caacttcatc cgaagcatgg ccgcctacat    2220
cctcctgctg ttcctgctgc agatcaagga cagacacaac ggcaacatta tgctggacaa    2280
gaagggtcat atcatccaca tcgactttgg cttcatgttt gaaagctcgc cgggcggcaa    2340
tctcggctgg gaacccgaca tcaagctgac ggatgagatg gtgatgatca tgggggcaa    2400
gatggaggcc acacccttca gtggttcat ggagatgtgt gtccgaggct acctggctgt    2460
gcggccctac atggacgcgg tcgtctccct ggtcactctc atgttggaca cgggcctgcc    2520
ctgttttcgc ggccagacaa tcaagctctt gaagcacagg tttagccca acatgactga    2580
gcgcgaggct gcaaatttca tcatgaaggt catccagagc tgcttcctca gcaacaggag    2640
ccggacctac gacatgatcc agtactatca gaatgcatc ccctactgag aggggaccct    2700
tcgagggcct ctgccccatg tgcctcaaa gctgtcccac aatcatggag ccctgcgacc    2760
tccctgccct gccgccacat gcagtggagg agaggcctgt ggcccaaaga acctggtagc    2820
gcctcctggg gcagcacgtg ggtggcgcag ccttggtaac gccatggact gcagcgacaa    2880
tcaatggatg gtgctgtcta tgcacaggtg tgagtcctct gtttgcactg gacatattcc    2940
ctacctgtct tatttcatag gtacatgaag tattgtgtat aaaaaagag ataagattta    3000
accaacatca acaaaataaa acccaaaat agtgaaaaaa aaaaaaaaaaa aaaaaaaaaa    3060
aaaaaaaaaa aaaaaaaaaa aaaaaaaaaa aaaaaaaaa                         3100
```

<210> SEQ ID NO 5
<211> LENGTH: 3109
<212> TYPE: DNA
<213> ORGANISM: Homo sapiens

<400> SEQUENCE: 5

```
agctcagcca tgtgctgtgc tgggcgccca cggacccacc cacaggcctc tcctacttct      60
ccagcatgta cccgccgcac cctctcacgg cgcagtacgg ggtgaaagtc ctgcggtcct     120
tccctccgga cgccatcctc ttctacatcc cccagattgt gcaggccctc agatgggcta     180
tgtgcgggag tatattctgt gggcagcgtc taaatcccag cttctggcac accagttcat     240
ctggaacatg aagactaaca tttatctaga tgaagagggc caccagaaag accctgacat     300
cggcgacctc ctggatcagt tggtagagga gatcacaggc tccttgtccg gcccagcgaa     360
ggacttttac cagcgggagt ttgatttctt taacaagatc accaacgtgt cggctatcat     420
caagccctac cctaaaggcg acgagagaaa gaaggcttgt ctgtcggccc tgtctgaagt     480
gaaggtgcag ccgggctgct acctgcccag caaccctgag gccattgtgc tggacatcga     540
ctacaagtct gggaccccga tgcagagtgc tgcaaaagcc ccatatctgg ccaagttcaa     600
ggtgaagcga tgtggagtta gtgaacttga aaagaaggt ctgcggtgcc gctcagactc     660
cgaggatgag tgcagcacgc aggaggccga cggccagaag atctcctggc aggcagccat     720
cttcaaggtg ggagacgact gccggcagga catgctggcc ctgcagatca tcgacctctt     780
caagaacatc ttccagctgg tcggcctgga cctctttgtt tttccctacc gcgtggtggc     840
cactgccccct gggtgcgggg tgatcgagtg catccccgac tgcacctccc gggaccagct     900
gggccgccag acagacttcg gcatgtacga ctacttcaca cgccagtacg gggatgagtc     960
cactctggcc ttccagcagc atggccgcct acagcctcct gctgttcctg ctgcagatca    1020
aggacagaca caacggcaac attatgctgg acaagaaggg tcatatcatc cacatcggtc    1080
agccagccac agcgccaccc tcctctccct tcacccctgg cacccagggg tggatagga    1140
tccccacccc acagagagga gaatgcccag gaccaccctg ccaggagtgt cagggtccag    1200
ctctgaggtc cgaactgtcg gccaccaagc tgttctgctg tagagggtgc ctggccccgg    1260
ccccagggag ctagggcgag agccgccatt gctctgagtc agaagctgga gctgggcgga    1320
gtggggctgg tccaggttca gtgccccagc ttggctcctt cctccacttc ctcccttctc    1380
tttctctgcc tgctgcccca ccacccaccc catcactgtc tccaagaaaa cacaacctgc    1440
ctgttggggg tggagggggt gctcctgttg cagtccttt ccactcctca aaacagacca    1500
cttgtccttg cccgccctgg ctcctaccca gtcacaggca gctctttggg gttttgcaga    1560
cttt ggcttc atgtttgaaa gctcgccggg cggcaatctc ggctgggaac ccgacatcaa    1620
gctgacggat gagatggtga tgatcatggg gggcaagatg gaggccacac ccttcaagtg    1680
gttcatggag atgtgtgtcc gaggctacct ggctgtgcgg tgagcctggg tgagggccag    1740
ggtggaggcg gaggggtgt gtggaacgtt ctgagatccc ctttaggatg aagggaatcc    1800
ggttccagag agtgaggtag gtgctagcag ccacctgctg acctacacct gtcctttggt    1860
cacctctgtc tgcccacctg tgccagtaaa ttcttgctct ggacatctaa ttccaaccac    1920
cttccccacg atcctgccca cgccttcagc catgggctct cccttctgg gcatcccatc    1980
caccctgtca ccaaagcctg agcacctgcc accccacagg ctacgtgcca aagatgggct    2040
ttgtcccagt ttcatataca ggtcacttgg ccaaggccac agtccaacct gggttcatcc    2100
ccactgcccct gcagagaaag gcaggtcagc gtgtctgcat cccacccaag tgcagaagcc    2160
atggccggca gccttatgtg ggggacaggg caggacactc agcctgtcca gagtgcgtgt    2220
gggcagccct tgcctgggcg gtatgggtta ccaagtgcag cagatcgaaa gttgcctcgg    2280
ggatgtgcaa gatgtggcag gcgaggtggg tggcaggagc ccacacctga ggctgttggc    2340
```

| | | |
|---|---|---|
| atcagccagt ccacaggact acaggcaggg ccaccaccta ggctggcctc agcccaccgc | 2400 | |
| tccctcctat ctctccccag gccctacatg gacgcggtcg tctccctggt cactctcatg | 2460 | |
| ttggacacgg gcctgccctg ttttcgcggc cagacaatca agctcttgaa gtacatttcc | 2520 | |
| agggcgtggc tctcagctga agtccgtccc catggaagac cctcctccca ctgggccagg | 2580 | |
| gagccagcac ggccctgccc atggcagccc tgacacagcc tctcccccag gcacaggttt | 2640 | |
| agccccaaca tgactgagcg cgaggctgca aatttcatca tgaaggtcat ccagagctgc | 2700 | |
| ttcctcagca acaggagccg gacctacgac atgatccagt actatcagaa tgacatcccc | 2760 | |
| tactgaggag gggaccttcg agggcctctg ccccatgtgc cctcaaagct gtcccacaat | 2820 | |
| catggagccc tgcgacctcc ctgccctgcc gccacatgca gtggaggaga ggcctgtggc | 2880 | |
| ccaaagaacc tggtagcgcc tcctggggca gcacgtgggt ggcgcagcct ggtaacgcc | 2940 | |
| atggactgca gcgacaatca atggatggtg ctgtctatgc acaggtgtga gtcctctgtt | 3000 | |
| tgcactggac atattcccta cctgtcttat ttcataggta catgaagtat tgtgtataaa | 3060 | |
| aaaagagata agattcaacc aacatcaaca aaataaaaac ccaaaatag | 3109 | |

<210> SEQ ID NO 6
<211> LENGTH: 3925
<212> TYPE: DNA
<213> ORGANISM: Homo sapiens

<400> SEQUENCE: 6

| | | |
|---|---|---|
| aaaaccatca gatctcctga gaactcattc gctgtcatga gatcaacaag ggggaaccgt | 60 | |
| ccccatgatc cagtcacctc ccaccaggtc tcttcctcaa cacctgagga ttacaattca | 120 | |
| agatgacatt tgggtgggga cacaaaacct aatcatatca gtgtgtcagt ttgtgaagga | 180 | |
| ggtatctctg catgtttctg gaacctgtct gtcactttgg aacattgttc taaacaacca | 240 | |
| gctcacaagt gagttttttag tacccagcct gcttttttctc gtacttgaca actccagaaa | 300 | |
| ttggtttgag agttgtgctt cttaaaccca tgggaagaca cagaggagac aaaggctgac | 360 | |
| tgtcgcccgc tttgcaaccc tgccccccag gtcccagccc ccagccagct ggaacttggc | 420 | |
| ctggccactg gctggactca acatcaatcc tggagagctt gtccacacca ctagagccac | 480 | |
| cgggccttac ccttgcctgg tctaccaaat gccgggagtc agcagctgct gacaaggccc | 540 | |
| tcctcatgga gagggccgag cctggctgac agggaccttg ctctcctgca gatgggctat | 600 | |
| gtgcgggagt atattctgtg ggcagcgtct aaatcccagc ttctggcaca ccagttcatc | 660 | |
| tggaacatga agactaacat ttatctagat gaagagggcc accagaaaga ccctgacatc | 720 | |
| ggcgacctcc tggatcagtt ggtagaggag atcacaggct ccttgtccgg cccagcgaag | 780 | |
| gactttttacc agcgggagtt tgatttcttt aacaagatca ccaacgtgtc ggctatcatc | 840 | |
| aagccctacc ctaaaggcga cgagagaaag aaggcttgtc tgtcggccct gtctgaagtg | 900 | |
| aaggtgcagc cgggctgcta cctgcccagc aaccctgagg ccattgtgct ggacatcgac | 960 | |
| tacaagtctg ggaccccgat gcagagtgct gcaaaagccc catatctggc caagttcaag | 1020 | |
| gtgaagcgat gtggagttag tgaacttgaa aagaaggtc tgcggtgccg ctcagactcc | 1080 | |
| gaggatgagt gcagcacgca ggaggccgac ggccagaaga tctcctggca ggcagccatc | 1140 | |
| ttcaaggtgg agacgactg ccggcaggta agcagggtca ggcctcgagt aggcttgggg | 1200 | |
| actgggcttg ctgctcccca aggctccagg cccgccagag tccaatctca tatgcagaaa | 1260 | |
| tgtgaatctt ttccttctct tatatggttc aggtgccacg gggtaaatta gggcttctgc | 1320 | |
| aaaacccaga ggcctctcct tccagcccct ttcccactgt ccccgccatg ccagtgccca | 1380 | |

```
cctgagggaa ctgtccaggg gttgggtgcc ttatctcaca caccccacca gacagctcag    1440
cctcatgctc agcccagggc ctggtggtcc cagcagcctg agtccagccc ccggtggtca    1500
gaaaggaagg ccttccagac tcttgctcgg ctgtggtctc cccacctcac tccatctctg    1560
ggtgcttggc ttttgccctg catgagccag aagagctgct ggggtgcaag gacgccaact    1620
gaccgcatcc tgcgcctccc ggcttcccag gacatgctgg ccctgcagat catcgacctc    1680
ttcaagaaca tcttccagct ggtcggcctg gacctctttg ttttttccta ccgcgtggtg    1740
gccactgccc ctgggtgcgg ggtgatcgag tgcatccccg actgcacctc ccggaccag    1800 ctgggccgcc agacagactt cggcatgtac gactacttca cacgccagta cggggatgag    1860
tccactctgg ccttccagca ggcccgctac aacttcatcc gaagcatggc cgcctacagc    1920
ctcctgctgt tcctgctgca gatcaaggac agacacaacg gcaacattat gctgacaag    1980 aagggtcata tcatccacat cggtcagcca gccacagcgc caccctcctc tcccttcacc    2040
cctggcaccc aggggtggat agggatcccc accccacaga gaggagaatg cccaggacca    2100
ccctgccagg agtgtcaggg tccagctctg aggtccgaac tgtcggccac caagctgttc    2160
tactgtagag ggtgcctggc cccggcccca gggagctagg gcgagagccg ccattgctct    2220
gagtcagaag ctggagctgg gcggagtggg gctggtccag gttcagtgcc ccagcttggc    2280
tccttcctcc acttcctccc ttctctttct ctgcctgctg ccccaccacc caccccatca    2340
ctgtctccaa gaaaacacaa cctgcctgtt ggggtggag gggtgctcc tgttgcagtc    2400 cttttccact cctcaaaaca gaccacttgt ccttgcccgc cctggctcct acccagtcac    2460
aggcagctct ttgggtttt gcagactttg gcttcatgtt tgaaagctcg ccgggcggca    2520
atctcggctg ggaacccgac atcaagctga cggatgagat ggtgatgatc atgggggca    2580 agatggaggc cacacccttc aagtggttca tggagatgtg tgtccgaggc tacctggctg    2640
tgcggtgagc ctgggtgagg gccagggtgg aggcggaggg ggtgtgtgga acgttctgag    2700
atccccttta ggatgaaggg aatccggttc cagagagtga ggtaggtgct agcagccacc    2760
tgctgaccta cacctgtcct ttggtcacct ctgtctgccc acctgtgcca gtaaattctt    2820
gctctggaca tctaattcca accaccttcc ccacgatcct gcccacgcct tcagccatgg    2880
gctctccctt tctgggcatc ccatccaccc tgtcaccaaa gcctgagcac ctgccacccc    2940
acaggctacg tgccaaagat gggctttgtc ccagtttcat atacaggtca cttggccaag    3000
gccacagtcc aacctgggtt catccccact gccctgcaga gaaaggcagg tcagcgtgtc    3060
tgcatcccac ccaagtgcag aagccatggc cagcagcctt atgtggggga cagggcagga    3120
cactcagcct gtccagagtg cgtgtgggca gcccttgcct gggcggtatg ggttaccaag    3180
tgcagcagat cgaaagttgc ctcggggatg tgcaagatgt ggcaggcgag gtgggtggca    3240
ggagcccaca cctgaggctg ttggcatcag ccagtccaca ggactacagg cagggccacc    3300
acctaggctg gcctcagccc accgctccct cctatctctc cccaggccct acatggacgc    3360
ggtcgtctcc ctggtcactc tcatgttgga cacgggcctg ccctgttttc gcggccagac    3420
aatcaagctc ttgaagcaca ggtttagccc caacatgact gagcgcgagg ctgcaaattt    3480
catcatgaag gtcatccaga gctgcttcct cagcaacagg agccggacct acgacatgat    3540
ccagtactat cagaatgaca tccctactg aggaggggac cttcgagggc ctctgcccca    3600
tgtgccctca agctgtccc acaatcatgg agccctgcga cctccctgcc ctgccgccac    3660
atgcagtgga ggagaggcct gtggcccaaa gaacctggta cgcgcctcctg gggcagcacg    3720 tgggtggcgc agccttggta acgccatgga ctgcagcgac aatcaatgga tggtgctgtc    3780
```

-continued

| | |
|---|---|
| tatgcacagg tgtgagtcct ctgtttgcac tggacatatt ccctacctgt cttatttcat | 3840 |
| aggtacatga agtattgtgt ataaaaaaag agataagatt taaccaacat caacaaaata | 3900 |
| aaaacccaaa atagtgctgt gttgg | 3925 |

<210> SEQ ID NO 7
<211> LENGTH: 6711
<212> TYPE: DNA
<213> ORGANISM: Homo sapiens

<400> SEQUENCE: 7

| | |
|---|---|
| gggcgctcgc gggccaggag cggggagccg gcgggcagcg ccgcggctcg tgaggtgatg | 60 |
| gcggcggccc cggcccgggg aggcggaggc ggaggcggag gcggcggcgg ctgctccggc | 120 |
| tccggctcca gcgcctcgcg gggcttctat ttcaacacgg tcctgtcact ggcccgctcc | 180 |
| ctggcggtgc agagaccagc atccttggag aaggtccaaa agcttctttg catgtgtcca | 240 |
| gtggatttcc atgggatctt ccagttagat gaaagacgga gagatgcagt gattgcattg | 300 |
| ggcattttc tgattgaatc tgatcttcag cacaaagatt gtgtggttcc ttaccttctt | 360 |
| cgacttctca aaggtcttcc aaaagtgtat tgggtagaag aaagcacagc tcggaaaggc | 420 |
| agaggtgccc tcccggttgc agagagcttc agcttctgct tggtaactct gctgtctgat | 480 |
| gtggcctata gggatccttc acttaggat gagattttag aggtgctttt gcaggttttg | 540 |
| catgtcctct tggggatgtg ccaggccttg agattcaag acaaagaata cctttgcaag | 600 |
| tatgctatcc catgcctgat aggaatctcg cgagcatttg ggcgttacag caacatggaa | 660 |
| gagtctctcc tctcaaagct cttccccaaa atccctcctc attccctccg tgtcctggaa | 720 |
| gagcttgaag tgttcgaag gcgttccttt aatgacttcc gctccatcct ccccagcaat | 780 |
| ctgctgactg tctgtcagga gggtacctg aagaggaaaa ccagcagtgt gtccagcatc | 840 |
| tctcaggtca gccctgaacg cggcatgccc cctcccagtt ccctggagg atctgccttt | 900 |
| cactactttg aagcctcctg cttgcccgat gggactgccc tagagcctga gtactacttt | 960 |
| tcaaccatca gctccagctt ctcagtctct ccccttttca cggtgtcac atataaggag | 1020 |
| tttaacattc cattggaaat gcttcgggaa ctcttaaacc tggtgaagaa gatcgttgag | 1080 |
| gaggctgttc tcaaatcttt ggatgccatt gtagccagtg tgatggaggc caaccccagt | 1140 |
| gctgatctct actacacttc cttcagtgac cctctctacc tgaccatgtt caagatgctg | 1200 |
| cgtgacactc tgtactacat gaaggacctc ccgacctctt ttgtgaagga gatccatgat | 1260 |
| tttgtgctgg agcagttcaa cacgagccag ggggagctcc agaagattct acatgacgca | 1320 |
| gaccggatcc acaatgagct gagccccctc aaactgcgct gtcaggcgaa tgctgcctgt | 1380 |
| gtggacctca tggtgtgggc tgtgaaggac gagcagggtg cagaaaacct ttgcatcaag | 1440 |
| ctatctgaga agctgcagtc caagacgtcc agcaaagtca ttattgctca cttgcccctg | 1500 |
| ctgatctgct gtctgcaggg tttgggccgc ctgtgcgaga ggttcccggt ggtggtgcac | 1560 |
| tctgtgacac cgtccttgcg agacttcctg gtcatcccgt ccccagttct ggtgaagctc | 1620 |
| tacaagtacc acagtcagta ccacacagtt gctggcaatg atataaaaat cagtgtgacc | 1680 |
| aatgagcatt ccgagtcaac cctgaacgtc atgtcgggta agaagagcca gccctccatg | 1740 |
| tacgagcagc tccgagacat cgctattgac aacatctgca ggtgcctgaa ggctggattg | 1800 |
| acggtggacc cagtgattgt ggaggcgttc ttggccagcc tgtccaaccg gctctacatc | 1860 |
| tctcaggaga gcgacaagga cgctcacttg attcccgacc acacaatccg agccttggga | 1920 |
| cacattgcgg tggccttgag ggacacccg aaggtcatgg agcccattct gcagatccta | 1980 |

```
cagcagaaat tctgccagcc accctccccc ctcgatgtgc tgattattga ccagctgggc    2040
tgcctggtta tcaccggaaa tcaatacatc tatcaggaag tgtggaacct cttccagcag    2100
atcagtgtga aggccagctc cgttgtatac tcagccacca agattacaa ggaccacggc     2160 tataggcatt gctccctggc agtgattaat gccctggcca acatcgcggc caacatccaa    2220
gacgagcacc tggtggatga gctgctcatg aacctgttgg agttgtttgt gcagctgggg    2280 ctggaggga agcgagccag cgagagggca agcgagaagg gccctgccct aaaggcttct     2340
agcagtgcag ggaacttggg agtactcatt cctgtaatag ctgtgctcac ccgacgactg    2400
ccacccatca agaagctaa gcctcggtta cagaagctct ccgagactt ctggctgtat      2460 tccgttctga tgggattcgc tgtggagggc tcaggactct ggccagaaga atggtacgag    2520
ggggtctgtg aaatagccac taagtcccc ttgctcacct ttcccagcaa ggagccactg     2580
cggtccgtcc tccagtataa ctcagccatg aagaatgaca cggtcacccc cgctgagctg    2640
agtgagctcc gcagcactat catcaacctg ctggacccc ctcccgaggt gtccgcactc     2700
atcaacaagc tggacttcgc catgtccacc tacctcctct ctgtgtaccg gctggagtac    2760
atgagggtac tgcgttcaac agatcctgat cgcttccagg taatgttctg ctactttgag    2820
gataaagcta ttcagaaaga caaatctggg atgatgcagt gtgtgattgc agtcgcggac    2880
aaagtattcg atgccttcct gaacatgatg gcggataaag ccaagaccaa ggagaacgag    2940
gaggagctgg agcggcacgc tcagttcctg ttggtgaact tcaaccacat ccacaagagg    3000
ataaggaggg tggcagacaa gtatctatct ggtctggtgg ataagtttcc ccacttgctc    3060
tggagcggga ctgtgctgaa gaccatgctg gacatcctgc agaccctgtc actgtcactg    3120
agcgctgata ttcacaagga tcagccttac tatgacatcc ccgacgcccc ctaccggatc    3180
acggttcctg acacgtacga agcccgtgag agcattgtga aggacttcgc tgcacgctgt    3240
gggatgatcc tccaggaggc catgaagtgg gcacctaccg tcaccaagtc ccacctgcag    3300
gaatatctga acaaacatca gaactgggta tcgggactgt cccagcacac ggggctggcc    3360
atggccactg agagcatcct tcactttgct ggctacaaca gcagaacac aactcttggg    3420 gcaactcagc tgagcgagcg cccggcctgt gtgaagaaag actactccaa cttcatggca    3480
tccctgaatc tgcgcaaccg ctacgcgggc gaggtgtatg aatgattcg gttctcaggc    3540 accacaggcc agatgtctga cctgaacaaa atgatggtcc aggatctaca ttcagcttta    3600
gaccgcagtc atcctcagca ctacacgcag gccatgttca agctgaccgc aatgctcatt    3660
agcagtaaag attgtgaccc gcagctcctt catcatctgt gctggggtcc cctccggatg    3720
ttcaatgagc atggcatgga gacggccctg gcctgctggg agtggctgct ggctggcaag    3780
gatggagtgg aagtgccgtt catgcgggag atggcagggg cctggcacat gacggtggag    3840
cagaaatttg gcctgttttc tgctgagata aaggaagcag accccctggc tgcctcggaa    3900
gcaagtcaac ccaaaccctg tcccccgaa gtgaccccc actacatctg gatcgacttc      3960
ctggtgcagc ggtttgagat cgccaagtac tgcagctctg accaagtgga gatcttctcc    4020
agcctgctgc agcgctccat gtccctgaac atcgcgggg ccaaggggag catgaaccgg     4080
cacgtggcgg ccatcgggcc ccgcttcaag ctgctgaccc tggggctgtc cctcctgcat    4140
gccgatgtgg ttcaaaatgc aaccatccgc aatgtgcttc gcgagaagat ctactccact    4200
gcctttgact acttcagctg tccccccaaag ttccctactc aaggagagaa gcggctgcgt   4260
gaagacataa gcatcatgat taaattttgg accgccatgt tctcagataa gaagtacctg    4320
accgccagcc agcttgttcc cccagataat caggacaccc ggagcaacct ggacataact    4380
```

```
gtcggctctc ggcaacaagc cacccaaggc tggatcaaca catacccct gtccagcggc    4440
atgtccacca tctccaagaa atcaggcatg tctaagaaaa ccaaccgggg ctcccagctg    4500
cacaaatact acatgaagcg caggacgctg ctgctgtccc tgctggccac tgagatcgag    4560
cgtctcatca catggtacaa cccgctgtca gccccggaac tggaactaga ccaggccgga    4620
gagaacagcg tggccaactg gagatctaag tacatcagcc tgagtgagaa gcagtggaag    4680
gacaacgtga acctcgcctg gagcatctct ccctacctag ccgtgcagct gcctgccagg    4740
tttaagaaca cagaagccat tgggaacgaa gtgacccgtc tcgttcggtt ggacccggga    4800
gccgttagtg atgtgcctga agcaatcaag ttcctggtca cctggcacac catcgacgcc    4860
gatgctccag agctcagcca tgtgctgtgc tgggcgccca cggacccacc cacaggcctc    4920
tcctacttct ccagcatgta cccgccgcac cctctcacgg cgcagtacgg ggtgaaagtc    4980
ctgcggtcct tccctccgga cgccatcctc ttctacatcc cccagattgt gcaggccctc    5040
aggtacgaca agatgggcta tgtgcgggag tatattctgt gggcagcgtc taaatcccag    5100
cttctggcac accagttcat ctggaacatg aagactaaca tttatctaga tgaagagggc    5160
caccagaaag accctgacat cggcgacctc ctggatcagt tggtagagga gatcacaggc    5220
tccttgtccg gcccagcgaa ggacttttac cagcgggagt ttgatttctt taacaagatc    5280
accaacgtgt cggctatcat caagccctac cctaaaggcg acgagagaaa gaaggcttgt    5340
ctgtcggccc tgtctgaagt gaaggtgcag ccgggctgct acctgcccag caaccctgag    5400
gccattgtgc tggacatcga ctacaagtct gggaccccga tgcagagtgc tgcaaaagcc    5460
ccatatctgg ccaagttcaa ggtgaagcga tgtggagtta gtgaacttga aaagaaggt    5520
ctgcggtgcc gctcagactc cgaggatgag tgcagcacgc aggaggccga cggccagaag    5580
atctcctggc aggcagccat cttcaaggtg ggagacgact gccggcagga catgctggcc    5640
ctgcagatca tcgacctctt caagaacatc ttccagctgg tcggcctgga cctctttgtt    5700
tttccctacc gcgtggtggc cactgcccct gggtgcgggg tgatcgagtg catccccgac    5760
tgcacctccc gggaccagct gggccgccag acagacttcg gcatgtacga ctacttcaca    5820
cgccagtacg gggatgagtc cactctggcc ttccagcagg cccgctacaa cttcatccga    5880
agcatggccg cctacagcct cctgctgttc ctgctgcaga tcaaggacag acacaacggc    5940
aacattatgc tggacaagaa gggtcatatc atccacatcg actttggctt catgtttgaa    6000
agctcgccgg gcggcaatct cggctgggaa cccgacatca agctgacgga tgagatggtg    6060
atgatcatgg ggggcaagat ggaggccaca cccttcaagt ggttcatgga gatgtgtgtc    6120
cgaggctacc tggctgtgcg gccctacatg gacgcggtcg tctccctggt cactctcatg    6180
ttggacacgg gcctgccctg ttttcgcggc cagacaatca agctcttgaa gcacaggttt    6240
agccccaaca tgactgagcg cgaggctgca aatttcatca tgaaggtcat ccagagctgc    6300
ttcctcagca acaggagccg gacctacgac atgatccagt actatcagaa tgacatcccc    6360
tactgaggag gggaccttcg agggcctctg ccccatgtgc cctcaaagct gtcccacaat    6420
catggagccc tgcgacctcc ctgccctgcc gccacatgca gtggaggaga ggcctgtggc    6480
ccaaagaacc tggtagcgcc tcctggggca gcacgtgggt ggcgcagcct tggtaacgcc    6540
atggactgca gcgacaatca atggatggtg ctgtctatgc acaggtgtga gtcctctgtt    6600
tgcactggac atattcccta cctgtcttat ttcataggta catgaagtat tgtgtataaa    6660
aaagagata agatttaacc aacatcaaca aaataaaaac ccaaaatagt g              6711
```

```
<210> SEQ ID NO 8
<211> LENGTH: 2044
<212> TYPE: PRT
<213> ORGANISM: Homo sapiens

<400> SEQUENCE: 8

Met Cys Pro Val Asp Phe His Gly Ile Phe Gln Leu Asp Glu Arg Arg
1               5                   10                  15

Arg Asp Ala Val Ile Ala Leu Gly Ile Phe Leu Ile Glu Ser Asp Leu
            20                  25                  30

Gln His Lys Asp Cys Val Val Pro Tyr Leu Leu Arg Leu Leu Lys Gly
        35                  40                  45

Leu Pro Lys Val Tyr Trp Val Glu Glu Ser Thr Ala Arg Lys Gly Arg
    50                  55                  60

Gly Ala Leu Pro Val Ala Glu Ser Phe Ser Phe Cys Leu Val Thr Leu
65                  70                  75                  80

Leu Ser Asp Val Ala Tyr Arg Asp Pro Ser Leu Arg Asp Glu Ile Leu
                85                  90                  95

Glu Val Leu Leu Gln Val Leu His Val Leu Gly Met Cys Gln Ala
            100                 105                 110

Leu Glu Ile Gln Asp Lys Glu Tyr Leu Cys Lys Tyr Ala Ile Pro Cys
        115                 120                 125

Leu Ile Gly Ile Ser Arg Ala Phe Gly Arg Tyr Ser Asn Met Glu Glu
    130                 135                 140

Ser Leu Leu Ser Lys Leu Phe Pro Lys Ile Pro Pro His Ser Leu Arg
145                 150                 155                 160

Val Leu Glu Glu Leu Glu Gly Val Arg Arg Arg Ser Phe Asn Asp Phe
                165                 170                 175

Arg Ser Ile Leu Pro Ser Asn Leu Leu Thr Val Cys Gln Glu Gly Thr
            180                 185                 190

Leu Lys Arg Lys Thr Ser Ser Val Ser Ser Ile Ser Gln Val Ser Pro
        195                 200                 205

Glu Arg Gly Met Pro Pro Ser Ser Pro Gly Gly Ser Ala Phe His
    210                 215                 220

Tyr Phe Glu Ala Ser Cys Leu Pro Asp Gly Thr Ala Leu Glu Pro Glu
225                 230                 235                 240

Tyr Tyr Phe Ser Thr Ile Ser Ser Phe Ser Val Ser Pro Leu Phe
                245                 250                 255

Asn Gly Val Thr Tyr Lys Glu Phe Asn Ile Pro Leu Glu Met Leu Arg
            260                 265                 270

Glu Leu Leu Asn Leu Val Lys Lys Ile Val Glu Glu Ala Val Leu Lys
        275                 280                 285

Ser Leu Asp Ala Ile Val Ala Ser Val Met Glu Ala Asn Pro Ser Ala
    290                 295                 300

Asp Leu Tyr Tyr Thr Ser Phe Ser Asp Pro Leu Tyr Leu Thr Met Phe
305                 310                 315                 320

Lys Met Leu Arg Asp Thr Leu Tyr Tyr Met Lys Asp Leu Pro Thr Ser
                325                 330                 335

Phe Val Lys Glu Ile His Asp Phe Val Leu Glu Gln Phe Asn Thr Ser
            340                 345                 350

Gln Gly Glu Leu Gln Lys Ile Leu His Asp Ala Asp Arg Ile His Asn
        355                 360                 365

Glu Leu Ser Pro Leu Lys Leu Arg Cys Gln Ala Ser Ala Ala Cys Val
    370                 375                 380

Asp Leu Met Val Trp Ala Val Lys Asp Glu Gln Gly Ala Glu Asn Leu
```

```
            385                 390                 395                 400
Cys Ile Lys Leu Ser Glu Lys Leu Gln Ser Lys Thr Ser Ser Lys Val
                405                 410                 415
Ile Ile Ala His Leu Pro Leu Ile Cys Cys Leu Gln Gly Leu Gly
                420                 425             430
Arg Leu Cys Glu Arg Phe Pro Val Val His Ser Val Thr Pro Ser
            435                 440                 445
Leu Arg Asp Phe Leu Val Ile Pro Ser Pro Val Leu Val Lys Leu Tyr
    450                 455                 460
Lys Tyr His Ser Gln Tyr His Thr Val Ala Gly Asn Asp Ile Lys Ile
465                 470                 475                 480
Ser Val Thr Asn Glu His Ser Glu Ser Thr Leu Asn Val Met Ser Gly
                485                 490                 495
Lys Lys Ser Gln Pro Ser Met Tyr Glu Gln Leu Arg Asp Ile Ala Ile
                500                 505                 510
Asp Asn Ile Cys Arg Cys Leu Lys Ala Gly Leu Thr Val Asp Pro Val
            515                 520                 525
Ile Val Glu Ala Phe Leu Ala Ser Leu Ser Asn Arg Leu Tyr Ile Ser
    530                 535                 540
Gln Glu Ser Asp Lys Asp Ala His Leu Ile Pro Asp His Thr Ile Arg
545                 550                 555                 560
Ala Leu Gly His Ile Ala Val Ala Leu Arg Asp Thr Pro Lys Val Met
                565                 570                 575
Glu Pro Ile Leu Gln Ile Leu Gln Gln Lys Phe Cys Gln Pro Pro Ser
                580                 585                 590
Pro Leu Asp Val Leu Ile Ile Asp Gln Leu Gly Cys Leu Val Ile Thr
        595                 600                 605
Gly Asn Gln Tyr Ile Tyr Gln Glu Val Trp Asn Leu Phe Gln Gln Ile
        610                 615                 620
Ser Val Lys Ala Ser Ser Val Val Tyr Ser Ala Thr Lys Asp Tyr Lys
625                 630                 635                 640
Asp His Gly Tyr Arg His Cys Ser Leu Ala Val Ile Asn Ala Leu Ala
                645                 650                 655
Asn Ile Ala Ala Asn Ile Gln Asp Glu His Leu Val Asp Glu Leu Leu
            660                 665                 670
Met Asn Leu Leu Glu Leu Phe Val Gln Leu Gly Leu Glu Gly Lys Arg
            675                 680                 685
Ala Ser Glu Arg Ala Ser Glu Lys Gly Pro Ala Leu Lys Ala Ser Ser
    690                 695                 700
Ser Ala Gly Asn Leu Gly Val Leu Ile Pro Val Ile Ala Val Leu Thr
705                 710                 715                 720
Arg Arg Leu Pro Pro Ile Lys Glu Ala Lys Pro Arg Leu Gln Lys Leu
                725                 730                 735
Phe Arg Asp Phe Trp Leu Tyr Ser Val Leu Met Gly Phe Ala Val Glu
                740                 745                 750
Gly Ser Gly Leu Trp Pro Glu Glu Trp Tyr Glu Gly Val Cys Glu Ile
            755                 760                 765
Ala Thr Lys Ser Pro Leu Leu Thr Phe Pro Ser Lys Glu Pro Leu Arg
    770                 775                 780
Ser Val Leu Gln Tyr Asn Ser Ala Met Lys Asn Asp Thr Val Thr Pro
785                 790                 795                 800
Ala Glu Leu Ser Glu Leu Arg Ser Thr Ile Ile Asn Leu Leu Asp Pro
                805                 810                 815
```

-continued

Pro Pro Glu Val Ser Ala Leu Ile Asn Lys Leu Asp Phe Ala Met Ser
            820                 825                 830

Thr Tyr Leu Leu Ser Val Tyr Arg Leu Glu Tyr Met Arg Val Leu Arg
            835                 840                 845

Ser Thr Asp Pro Asp Arg Phe Gln Val Met Cys Tyr Phe Glu Asp
850                 855                 860

Lys Ala Ile Gln Lys Asp Lys Ser Gly Met Met Gln Cys Val Ile Ala
865                 870                 875                 880

Val Ala Asp Lys Val Phe Asp Ala Phe Leu Asn Met Met Ala Asp Lys
                885                 890                 895

Ala Lys Thr Lys Glu Asn Glu Glu Leu Glu Arg His Ala Gln Phe
            900                 905                 910

Leu Leu Val Asn Phe Asn His Ile His Lys Arg Ile Arg Arg Val Ala
            915                 920                 925

Asp Lys Tyr Leu Ser Gly Leu Val Asp Lys Phe Pro His Leu Leu Trp
            930                 935                 940

Ser Gly Thr Val Leu Lys Thr Met Leu Asp Ile Leu Gln Thr Leu Ser
945                 950                 955                 960

Leu Ser Leu Ser Ala Asp Ile His Lys Asp Gln Pro Tyr Tyr Asp Ile
                965                 970                 975

Pro Asp Ala Pro Tyr Arg Ile Thr Val Pro Asp Thr Tyr Glu Ala Arg
            980                 985                 990

Glu Ser Ile Val Lys Asp Phe Ala Ala Arg Cys Gly Met Ile Leu Gln
            995                 1000                1005

Glu Ala Met Lys Trp Ala Pro Thr Val Thr Lys Ser His Leu Gln
    1010                1015                1020

Glu Tyr Leu Asn Lys His Gln Asn Trp Val Ser Gly Leu Ser Gln
    1025                1030                1035

His Thr Gly Leu Ala Met Ala Thr Glu Ser Ile Leu His Phe Ala
    1040                1045                1050

Gly Tyr Asn Lys Gln Asn Thr Thr Leu Gly Ala Thr Gln Leu Ser
    1055                1060                1065

Glu Arg Pro Ala Cys Val Lys Lys Asp Tyr Ser Asn Phe Met Ala
    1070                1075                1080

Ser Leu Asn Leu Arg Asn Arg Tyr Ala Gly Glu Val Tyr Gly Met
    1085                1090                1095

Ile Arg Phe Ser Gly Thr Thr Gly Gln Met Ser Asp Leu Asn Lys
    1100                1105                1110

Met Met Val Gln Asp Leu His Ser Ala Leu Asp Arg Ser His Pro
    1115                1120                1125

Gln His Tyr Thr Gln Ala Met Phe Lys Leu Thr Ala Met Leu Ile
    1130                1135                1140

Ser Ser Lys Asp Cys Asp Pro Gln Leu Leu His His Leu Cys Trp
    1145                1150                1155

Gly Pro Leu Arg Met Phe Asn Glu His Gly Met Glu Thr Ala Leu
    1160                1165                1170

Ala Cys Trp Glu Trp Leu Leu Ala Gly Lys Asp Gly Val Glu Val
    1175                1180                1185

Pro Phe Met Arg Glu Met Ala Gly Ala Trp His Met Thr Val Glu
    1190                1195                1200

Gln Lys Phe Gly Leu Phe Ser Ala Glu Ile Lys Glu Ala Asp Pro
    1205                1210                1215

Leu Ala Ala Ser Glu Ala Ser Gln Pro Lys Pro Cys Pro Pro Glu
    1220                1225                1230

```
Val Thr Pro His Tyr Ile Trp Ile Asp Phe Leu Val Gln Arg Phe
    1235                1240                1245

Glu Ile Ala Lys Tyr Cys Ser Ser Asp Gln Val Glu Ile Phe Ser
    1250                1255                1260

Ser Leu Leu Gln Arg Ser Met Ser Leu Asn Ile Gly Gly Ala Lys
    1265                1270                1275

Gly Ser Met Asn Arg His Val Ala Ala Ile Gly Pro Arg Phe Lys
    1280                1285                1290

Leu Leu Thr Leu Gly Leu Ser Leu Leu His Ala Asp Val Val Pro
    1295                1300                1305

Asn Ala Thr Ile Arg Asn Val Leu Arg Glu Lys Ile Tyr Ser Thr
    1310                1315                1320

Ala Phe Asp Tyr Phe Ser Cys Pro Pro Lys Phe Pro Thr Gln Gly
    1325                1330                1335

Glu Lys Arg Leu Arg Glu Asp Ile Ser Ile Met Ile Lys Phe Trp
    1340                1345                1350

Thr Ala Met Phe Ser Asp Lys Lys Tyr Leu Thr Ala Ser Gln Leu
    1355                1360                1365

Val Pro Pro Asp Asn Gln Asp Thr Arg Ser Asn Leu Asp Ile Thr
    1370                1375                1380

Val Gly Ser Arg Gln Gln Ala Thr Gln Gly Trp Ile Asn Thr Tyr
    1385                1390                1395

Pro Leu Ser Ser Gly Met Ser Thr Ile Ser Lys Lys Ser Gly Met
    1400                1405                1410

Ser Lys Lys Thr Asn Arg Gly Ser Gln Leu His Lys Tyr Tyr Met
    1415                1420                1425

Lys Arg Arg Thr Leu Leu Leu Ser Leu Leu Ala Thr Glu Ile Glu
    1430                1435                1440

Arg Leu Ile Thr Trp Tyr Asn Pro Leu Ser Ala Pro Glu Leu Glu
    1445                1450                1455

Leu Asp Gln Ala Gly Glu Asn Ser Val Ala Asn Trp Arg Ser Lys
    1460                1465                1470

Tyr Ile Ser Leu Ser Glu Lys Gln Trp Lys Asp Asn Val Asn Leu
    1475                1480                1485

Ala Trp Ser Ile Ser Pro Tyr Leu Ala Val Gln Leu Pro Ala Arg
    1490                1495                1500

Phe Lys Asn Thr Glu Ala Ile Gly Asn Glu Val Thr Arg Leu Val
    1505                1510                1515

Arg Leu Asp Pro Gly Ala Val Ser Asp Val Pro Glu Ala Ile Lys
    1520                1525                1530

Phe Leu Val Thr Trp His Thr Ile Asp Ala Asp Ala Pro Glu Leu
    1535                1540                1545

Ser His Val Leu Cys Trp Ala Pro Thr Asp Pro Thr Gly Leu
    1550                1555                1560

Ser Tyr Phe Ser Ser Met Tyr Pro Pro His Pro Leu Thr Ala Gln
    1565                1570                1575

Tyr Gly Val Lys Val Leu Arg Ser Phe Pro Asp Ala Ile Leu
    1580                1585                1590

Phe Tyr Ile Pro Gln Ile Val Gln Ala Leu Arg Tyr Asp Lys Met
    1595                1600                1605

Gly Tyr Val Arg Glu Tyr Ile Leu Trp Ala Ala Ser Lys Ser Gln
    1610                1615                1620

Leu Leu Ala His Gln Phe Ile Trp Asn Met Lys Thr Asn Ile Tyr
```

```
                      1625                1630                1635

Leu Asp  Glu  Glu  Gly  His  Gln  Lys  Asp  Pro  Asp  Ile  Gly  Asp  Leu
    1640                1645                1650

Leu Asp  Gln  Leu  Val  Glu  Glu  Ile  Thr  Gly  Ser  Leu  Ser  Gly  Pro
    1655                1660                1665

Ala Lys  Asp  Phe  Tyr  Gln  Arg  Glu  Phe  Asp  Phe  Phe  Asn  Lys  Ile
    1670                1675                1680

Thr Asn  Val  Ser  Ala  Ile  Ile  Lys  Pro  Tyr  Pro  Lys  Gly  Asp  Glu
    1685                1690                1695

Arg Lys  Lys  Ala  Cys  Leu  Ser  Ala  Leu  Ser  Glu  Val  Lys  Val  Gln
    1700                1705                1710

Pro Gly  Cys  Tyr  Leu  Pro  Ser  Asn  Pro  Glu  Ala  Ile  Val  Leu  Asp
    1715                1720                1725

Ile Asp  Tyr  Lys  Ser  Gly  Thr  Pro  Met  Gln  Ser  Ala  Ala  Lys  Ala
    1730                1735                1740

Pro Tyr  Leu  Ala  Lys  Phe  Lys  Val  Lys  Arg  Cys  Gly  Val  Ser  Glu
    1745                1750                1755

Leu Glu  Lys  Glu  Gly  Leu  Arg  Cys  Arg  Ser  Asp  Ser  Glu  Asp  Glu
    1760                1765                1770

Cys Ser  Thr  Gln  Glu  Ala  Asp  Gly  Gln  Lys  Ile  Ser  Trp  Gln  Ala
    1775                1780                1785

Ala Ile  Phe  Lys  Val  Gly  Asp  Asp  Cys  Arg  Gln  Asp  Met  Leu  Ala
    1790                1795                1800

Leu Gln  Ile  Ile  Asp  Leu  Phe  Lys  Asn  Ile  Phe  Gln  Leu  Val  Gly
    1805                1810                1815

Leu Asp  Leu  Phe  Val  Phe  Pro  Tyr  Arg  Val  Val  Ala  Thr  Ala  Pro
    1820                1825                1830

Gly Cys  Gly  Val  Ile  Glu  Cys  Ile  Pro  Asp  Cys  Thr  Ser  Arg  Asp
    1835                1840                1845

Gln Leu  Gly  Arg  Gln  Thr  Asp  Phe  Gly  Met  Tyr  Asp  Tyr  Phe  Thr
    1850                1855                1860

Arg Gln  Tyr  Gly  Asp  Glu  Ser  Thr  Leu  Ala  Phe  Gln  Gln  Ala  Arg
    1865                1870                1875

Tyr Asn  Phe  Ile  Arg  Ser  Met  Ala  Ala  Tyr  Ser  Leu  Leu  Leu  Phe
    1880                1885                1890

Leu Leu  Gln  Ile  Lys  Asp  Arg  His  Asn  Gly  Asn  Ile  Met  Leu  Asp
    1895                1900                1905

Lys Lys  Gly  His  Ile  Ile  His  Ile  Asp  Phe  Gly  Phe  Met  Phe  Glu
    1910                1915                1920

Ser Ser  Pro  Gly  Gly  Asn  Leu  Gly  Trp  Glu  Pro  Asp  Ile  Lys  Leu
    1925                1930                1935

Thr Asp  Glu  Met  Val  Met  Ile  Met  Gly  Gly  Lys  Met  Glu  Ala  Thr
    1940                1945                1950

Pro Phe  Lys  Trp  Phe  Met  Glu  Met  Cys  Val  Arg  Gly  Tyr  Leu  Ala
    1955                1960                1965

Val Arg  Pro  Tyr  Met  Asp  Ala  Val  Val  Ser  Leu  Val  Thr  Leu  Met
    1970                1975                1980

Leu Asp  Thr  Gly  Leu  Pro  Cys  Phe  Arg  Gly  Gln  Thr  Ile  Lys  Leu
    1985                1990                1995

Leu Lys  His  Arg  Phe  Ser  Pro  Asn  Met  Thr  Glu  Arg  Glu  Ala  Ala
    2000                2005                2010

Asn Phe  Ile  Met  Lys  Val  Ile  Gln  Ser  Cys  Phe  Leu  Ser  Asn  Arg
    2015                2020                2025
```

```
Ser Arg Thr Tyr Asp Met Ile Gln Tyr Tyr Gln Asn Asp Ile Pro
    2030            2035            2040
Tyr
```

PIK4CA AS MODIFIER OF THE RAC PATHWAY AND METHODS OF USE

REFERENCE TO RELATED APPLICATIONS

This application claims priority to U.S. provisional patent application 60/611,127 filed Sep. 17, 2004. The contents of the prior application are hereby incorporated in their entirety.

BACKGROUND OF THE INVENTION

Cell movement is an important part of normal developmental and physiological processes (e.g. epiboly, gastrulation and wound healing), and is also important in pathologies such as tumor progression and metastasis, angiogenesis, inflammation and atherosclerosis. The process of cell movement involves alterations of cell-cell and cell-matrix interactions in response to signals, as well as rearrangement of the actin and microtubule cytoskeletons. The small GTPases of the Rho/Rac family interact with a variety of molecules to regulate the processes of cell motility, cell-cell adhesion and cell-matrix adhesion. Cdc42 and Rac are implicated in the formation of filopodia and lamellipodia required for initiating cell movement, and Rho regulates stress fiber and focal adhesion formation. Rho/Rac proteins are effectors of cadherin/catenin-mediated cell-cell adhesion, and function downstream of integrins and growth factor receptors to regulate cytoskeletal changes important for cell adhesion and motility.

There are five members of the Rho/Rac family in the *C. elegans* genome. rho-1 encodes a protein most similar to human RhoA and RhoC, cdc-42 encodes an ortholog of human Cdc42, and ced-10, mig-2 and rac-2 encode Rac-related proteins. ced-10, mig-2 and rac-2 have partially redundant functions in the control of a number of cell and axonal migrations in the worm, as inactivation of two or all three of these genes causes enhanced migration defects when compared to the single mutants. Furthermore, ced-10; mig-2 double mutants have gross morphological and movement defects not seen in either single mutant, possibly as a secondary effect of defects in cell migration or movements during morphogenesis. These defects include a completely penetrant uncoordinated phenotype, as well as variably penetrant slow-growth, vulval, withered tail, and sterility defects, none of which are seen in either single mutant.

Phosphatidylinositol (PI) 4-Kinase (PIK4Ca) Catalyzes the First Committed Step in the Biosynthesis of Phosphatidylinositol 4,5-Bisphosphate. The Mammalian PI 4-Kinases have been Classified into Two Types, II and III, Based on their Molecular Mass, and Modulation by Detergent and Adenosine. Two Transcript Variants Encoding Different Isoforms have been Described for this Gene.

The ability to manipulate the genomes of model organisms such as *C. elegans* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Dulubova I, et al, J Neurochem 2001 April; 77(1):229-38; Cai T, et al., Diabetologia 2001 January; 44(1):81-8; Pasquinelli A E, et al., Nature. 2000 Nov. 2; 408(6808):37-8; Ivanov I P, et al., EMBO J 2000 Apr. 17; 19(8):1907-17; Vajo Z et al., Mamm Genome 1999 October; 10(10): 1000-4). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as RAC, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the RAC pathway in *C. elegans*, and identified their human orthologs, hereinafter referred to as PIK4CA. The invention provides methods for utilizing these RAC modifier genes and polypeptides to identify PIK4CA-modulating agents that are candidate therapeutic agents that can be used in the treatment of disorders associated with defective or impaired RAC function and/or PIK4CA function. Preferred PIK4CA-modulating agents specifically bind to PIK4CA polypeptides and restore RAC function. Other preferred PIK4CA-modulating agents are nucleic acid modulators such as antisense oligomers and RNAi that repress PIK4CA gene expression or product activity by, for example, binding to and inhibiting the respective nucleic acid (i.e. DNA or mRNA).

PIK4CA modulating agents may be evaluated by any convenient in vitro or in vivo assay for molecular interaction with a PIK4CA polypeptide or nucleic acid. In one embodiment, candidate PIK4CA modulating agents are tested with an assay system comprising a PIK4CA polypeptide or nucleic acid. Agents that produce a change in the activity of the assay system relative to controls are identified as candidate RAC modulating agents. The assay system may be cell-based or cell-free. PIK4CA-modulating agents include PIK4CA related proteins (e.g. dominant negative mutants, and biotherapeutics); PIK4CA-specific antibodies; PIK4CA-specific antisense oligomers and other nucleic acid modulators; and chemical agents that specifically bind to or interact with PIK4CA or compete with PIK4CA binding partner (e.g. by binding to a PIK4CA binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate RAC pathway modulating agents are further tested using a second assay system that detects changes in the RAC pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the RAC pathway, such as an angiogenic, apoptotic, or cell proliferation disorder (e.g. cancer).

The invention further provides methods for modulating the PIK4CA function and/or the RAC pathway in a mammalian cell by contacting the mammalian cell with an agent that specifically binds a PIK4CA polypeptide or nucleic acid. The agent may be a small molecule modulator, a nucleic acid modulator, or an antibody and may be administered to a mammalian animal predetermined to have a pathology associated with the RAC pathway.

DETAILED DESCRIPTION OF THE INVENTION

A genetic screen was designed to identify modifiers of the Rac signaling pathway that also affect cell migrations in *C. elegans*, where various specific genes were silenced by RNA inhibition (RNAi) in a ced-10; mig-2 double mutant background. Methods for using RNAi to silence genes in *C. elegans* are known in the art (Fire A, et al., 1998 Nature 391:806-811; Fire, A. Trends Genet. 15, 358-363 (1999); WO9932619). Genes causing altered phenotypes in the worms were identified as modifiers of the RAC pathway. A modifiers of particular interest, 3N342, was identified followed by identification of its orthologs. Accordingly, vertebrate orthologs of the modifier, and preferably the human orthologs, PIK4CA genes (i.e., nucleic acids and polypeptides) are attractive drug targets for the treatment of pathologies associated with a defective RAC signaling pathway, such as cancer.

In vitro and in vivo methods of assessing PIK4CA function are provided herein. Modulation of the PIK4CA or their respective binding partners is useful for understanding the association of the RAC pathway and its members in normal and disease conditions and for developing diagnostics and therapeutic modalities for RAC related pathologies. PIK4CA-modulating agents that act by inhibiting or enhancing PIK4CA expression, directly or indirectly, for example, by affecting a PIK4CA function such as enzymatic (e.g., catalytic) or binding activity, can be identified using methods provided herein. PIK4CA modulating agents are useful in diagnosis, therapy and pharmaceutical development.

Nucleic Acids and Polypeptides of the Invention

Sequences related to PIK4CA nucleic acids and polypeptides that can be used in the invention are disclosed in Genbank (referenced by Genbank identifier (GI) number) as GI#s 4505806 (SEQ ID NO: 1), 17105399 (SEQ ID NO:2), 17390265 (SEQ ID NO:3), 32197215 (SEQ ID NO:4), 21755146 (SEQ ID NO:5), 34530550 (SEQ ID NO:6), and 68533058 (SEQ ID NO:7) nucleic acid, and GI# 17105400 (SEQ ID NO:8) for polypeptides.

The term "PIK4CA polypeptide" refers to a full-length PIK4CA protein or a functionally active fragment or derivative thereof. A "functionally active" PIK4CA fragment or derivative exhibits one or more functional activities associated with a full-length, wild-type PIK4CA protein, such as antigenic or immunogenic activity, enzymatic activity, ability to bind natural cellular substrates, etc. The functional activity of PIK4CA proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active PIK4CA polypeptide is a PIK4CA derivative capable of rescuing defective endogenous PIK4CA activity, such as in cell based or animal assays; the rescuing derivative may be from the same or a different species. For purposes herein, functionally active fragments also include those fragments that comprise one or more structural domains of a PIK4CA, such as a kinase domain or a binding domain. Protein domains can be identified using the PFAM program (Bateman A., et al., Nucleic Acids Res, 1999, 27:260-2). For example, the kinase domain (PFAM 00613) of PIK4CA from GI# 17105400 (SEQ ID NO: 8) is located at approximately amino acid residues 1501 to 1670, and 1786 to 1993. Methods for obtaining PIK4CA polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a PIK4CA. In further preferred embodiments, the fragment comprises the entire functionally active domain.

The term "PIK4CA nucleic acid" refers to a DNA or RNA molecule that encodes a PIK4CA polypeptide. Preferably, the PIK4CA polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human PIK4CA. Methods of identifying orthologs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein.; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a PIK4CA. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a PIK4CA under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of PIK4CA Nucleic Acids and Polypeptides PIK4CA nucleic acids and polypeptides are useful for identifying and testing agents that modulate PIK4CA function and for other applications related to the involvement of PIK4CA in the RAC pathway. PIK4CA nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a PIK4CA protein for assays used to assess PIK4CA function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, N.J., 1996; Coligan J E et al, Current Protocols in Protein Science (eds.), 1999, John Wiley & Sons, New York). In particular embodiments, recombinant PIK4CA is expressed in a cell line known to have defective RAC function. The recombinant cells are used in cell-based screening assay systems of the invention, as described further below.

The nucleotide sequence encoding a PIK4CA polypeptide can be inserted into any appropriate expression vector. The necessary transcriptional and translational signals, including promoter/enhancer element, can derive from the native PIK4CA gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the PIK4CA gene product, the expression vector can comprise a promoter operably linked to a PIK4CA gene nucleic acid, one or more origins of replication, and, one or more selectable markers (e.g. thymidine kinase activity, resistance to antibiotics, etc.). Alternatively, recombinant expression vectors can be identified by assaying for the expression of the PIK4CA gene product based on the physical or functional properties of the PIK4CA protein in in vitro assay systems (e.g. immunoassays).

The PIK4CA protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the PIK4CA gene sequence is identified, the gene product can be isolated and purified using standard methods (e.g. ion exchange, affinity, and gel exclusion chromatography; centrifugation; differential solubility; electrophoresis). Alternatively, native PIK4CA proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of PIK4CA or other genes associated with the RAC pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter PIK4CA expression may be used in in vivo assays to test for activity of a candidate RAC modulating agent, or to further assess the role of PIK4CA in a RAC pathway process such as apoptosis or cell proliferation. Preferably, the altered PIK4CA expression results in a detectable phenotype, such as decreased or increased levels of cell proliferation, angiogenesis, or apoptosis compared to control animals having normal PIK4CA expression. The genetically modified animal may additionally have altered RAC expression (e.g. RAC knock-out). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous PIK4CA gene that results in a decrease of PIK4CA function, preferably such that PIK4CA expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse PIK4CA gene is used to construct a homologous recombination vector suitable for altering an endogenous PIK4CA gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the PIK4CA gene, e.g., by introduction of additional copies of PIK4CA, or by operatively inserting a regulatory sequence that provides for altered expression of an endogenous copy of the PIK4CA gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the RAC pathway, as animal models of disease and disorders implicating defective RAC function, and for in vivo testing of candidate therapeutic agents, such as those identified in screens described below. The candidate therapeutic agents are administered to a genetically modified animal having altered PIK4CA function and phenotypic changes are compared with appropriate control animals such as genetically modified animals that receive placebo treatment, and/or animals with unaltered PIK4CA expression that receive candidate therapeutic agent.

In addition to the above-described genetically modified animals having altered PIK4CA function, animal models having defective RAC function (and otherwise normal PIK4CA function), can be used in the methods of the present invention. For example, a RAC knockout mouse can be used to assess, in vivo, the activity of a candidate RAC modulating agent identified in one of the in vitro assays described below. Preferably, the candidate RAC modulating agent when administered to a model system with cells defective in RAC function, produces a detectable phenotypic change in the model system indicating that the RAC function is restored, i.e., the cells exhibit normal cell cycle progression.

Modulating Agents

The invention provides methods to identify agents that interact with and/or modulate the function of PIK4CA and/or the RAC pathway. Modulating agents identified by the methods are also part of the invention. Such agents are useful in a variety of diagnostic and therapeutic applications associated with the RAC pathway, as well as in further analysis of the PIK4CA protein and its contribution to the RAC pathway. Accordingly, the invention also provides methods for modulating the RAC pathway comprising the step of specifically modulating PIK4CA activity by administering a PIK4CA-interacting or -modulating agent.

As used herein, a "PIK4CA-modulating agent" is any agent that modulates PIK4CA function, for example, an agent that interacts with PIK4CA to inhibit or enhance PIK4CA activity or otherwise affect normal PIK4CA function. PIK4CA function can be affected at any level, including transcription, protein expression, protein localization, and cellular or extra-cellular activity. In a preferred embodiment, the PIK4CA-modulating agent specifically modulates the function of the PIK4CA. The phrases "specific modulating agent", "specifically modulates", etc., are used herein to refer to modulating agents that directly bind to the PIK4CA polypeptide or nucleic acid, and preferably inhibit, enhance, or otherwise alter, the function of the PIK4CA. These phrases also encompass modulating agents that alter the interaction of the PIK4CA with a binding partner, substrate, or cofactor (e.g. by binding to a binding partner of a PIK4CA, or to a protein/binding partner complex, and altering PIK4CA function). In a further preferred embodiment, the PIK4CA-modulating agent is a modulator of the RAC pathway (e.g. it restores and/or upregulates RAC function) and thus is also a RAC-modulating agent.

Preferred PIK4CA-modulating agents include small molecule compounds; PIK4CA-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the PIK4CA protein or may be identified by screening compound libraries. Alternative appropriate modulators of this class are natural products, particularly secondary metabolites from organisms such as plants or fungi, which can also be identified by screening compound libraries for PIK4CA-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the RAC pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific PIK4CA-interacting proteins are useful in a variety of diagnostic and therapeutic applications related to the RAC pathway and related disorders, as well as in validation assays for other PIK4CA-modulating agents. In a preferred embodiment, PIK4CA-interacting proteins affect normal PIK4CA function, including transcription, protein expression, protein localization, and cellular or extra-cellular activity. In another embodiment, PIK4CA-interacting proteins are useful in detecting and providing information about the function of PIK4CA proteins, as is relevant to RAC related disorders, such as cancer (e.g., for diagnostic means).

A PIK4CA-interacting protein may be endogenous, i.e. one that naturally interacts genetically or biochemically with a PIK4CA, such as a member of the PIK4CA pathway that modulates PIK4CA expression, localization, and/or activity. PIK4CA-modulators include dominant negative forms of PIK4CA-interacting proteins and of PIK4CA proteins themselves. Yeast two-hybrid and variant screens offer preferred methods for identifying endogenous PIK4CA-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928, 868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

A PIK4CA-interacting protein may be an exogenous protein, such as a PIK4CA-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). PIK4CA antibodies are further discussed below.

In preferred embodiments, a PIK4CA-interacting protein specifically binds a PIK4CA protein. In alternative preferred embodiments, a PIK4CA-modulating agent binds a PIK4CA substrate, binding partner, or cofactor.

Antibodies

In another embodiment, the protein modulator is a PIK4CA specific antibody agonist or antagonist. The antibodies have therapeutic and diagnostic utilities, and can be used in screening assays to identify PIK4CA modulators. The antibodies can also be used in dissecting the portions of the PIK4CA pathway responsible for various cellular responses and in the general processing and maturation of the PIK4CA.

Antibodies that specifically bind PIK4CA polypeptides can be generated using known methods. Preferably the antibody is specific to a mammalian ortholog of PIK4CA polypeptide, and more preferably, to human PIK4CA. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of PIK4CA which are particularly antigenic can be selected, for example, by routine screening of PIK4CA polypeptides for antigenicity or by applying a theoretical method for selecting antigenic regions of a protein (Hopp and Wood (1981), Proc. Nati. Acad. Sci. U.S.A. 78:3824-28; Hopp and Wood, (1983) Mol. Immunol. 20:483-89; Sutcliffe et al., (1983) Science 219:660-66) to the amino acid sequence of a PIK4CA. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of PIK4CA or substantially purified fragments thereof. If PIK4CA fragments are used, they preferably comprise at least 10, and more preferably, at least 20 contiguous amino acids of a PIK4CA protein. In a particular embodiment, PIK4CA-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of PIK4CA-specific antibodies is assayed by an appropriate assay such as a solid phase enzyme-linked immunosorbant assay (ELISA) using immobilized corresponding PIK4CA polypeptides. Other assays, such as radioimmunoassays or fluorescent assays might also be used.

Chimeric antibodies specific to PIK4CA polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323:323-327). Humanized antibodies contain 10% murine sequences and ~90% human sequences, and thus further reduce or eliminate immunogenicity, while retaining the antibody specificities (Co M S, and Queen C. 1991 Nature 351:501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

PIK4CA-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246:1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred PIK4CA-modulating agents comprise nucleic acid molecules, such as antisense oligomers or double stranded RNA (dsRNA), which generally inhibit PIK4CA activity. Preferred nucleic acid modulators interfere with the function of the PIK4CA nucleic acid such as DNA replication, transcription, translocation of the PIK4CA RNA to the site of protein translation, translation of protein from the PIK4CA RNA, splicing of the PIK4CA RNA to yield one or more mRNA species, or catalytic activity which may be engaged in or facilitated by the PIK4CA RNA.

In one embodiment, the antisense oligomer is an oligonucleotide that is sufficiently complementary to a PIK4CA mRNA to bind to and prevent translation, preferably by binding to the 5' untranslated region. PIK4CA-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphorodiamidate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g., see WO99/18193; Probst JC, Antisense Oligodeoxynucleotide and Ribozyme Design, (2000) Methods, 22(3):271-281; Summerton J, and Weller D. (1997) Antisense Nucleic Acid Drug Dev. 7:187-95; U.S. Pat. No. 5,235,033; and U.S. Pat. No. 5,378,841).

Alternative preferred PIK4CA nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178; Hsieh A C et al. (2004) NAR 32(3):893-901).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a PIK4CA-specific nucleic acid modulator is used in an assay to further elucidate the role of the PIK4CA in the RAC pathway, and/or its relationship to other members of the pathway. In another aspect of the invention, a PIK4CA-specific antisense oligomer is used as a therapeutic agent for treatment of RAC-related disease states.

Assay Systems

The invention provides assay systems and screening methods for identifying specific modulators of PIK4CA activity. As used herein, an, "assay system" encompasses all the components required for performing and analyzing results of an assay that detects and/or measures a particular event. In general, primary assays are used to identify or confirm a modulator's specific biochemical or molecular effect with respect to the PIK4CA nucleic acid or protein. In general, secondary assays further assess the activity of a PIK4CA modulating agent identified by a primary assay and may confirm that the modulating agent affects PIK4CA in a manner relevant to the RAC pathway. In some cases, PIK4CA modulators will be directly tested in a secondary assay.

In a preferred embodiment, the screening method comprises contacting a suitable assay system comprising a PIK4CA polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates PIK4CA activity, and hence the RAC pathway. The PIK4CA polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of PIK4CA and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when PIK4CA-interacting proteins are used in screens to identify small molecule modulators, the binding specificity of the interacting protein to the PIK4CA protein may be assayed by various known methods such as substrate processing (e.g. ability of the candidate PIK4CA-specific binding agents to function as negative effectors in PIK4CA-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit PIK4CA specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a PIK4CA polypeptide, a fusion protein thereof, or to cells or membranes bearing the polypeptide or fusion protein. The PIK4CA polypeptide can be full length or a fragment thereof that retains functional PIK4CA activity. The PIK4CA polypeptide may be fused to another polypeptide, such as a peptide tag for detection or anchoring, or to another tag. The PIK4CA polypeptide is preferably human PIK4CA, or is an ortholog or derivative thereof as described above. In a preferred embodiment, the screening assay detects candidate agent-based modulation of PIK4CA interaction with a binding target, such as an endogenous or exogenous protein or other substrate that has PIK4CA-specific binding activity, and can be used to assess normal PIK4CA gene function.

Suitable assay formats that may be adapted to screen for PIK4CA modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate PIK4CA and RAC pathway modulators (e.g. U.S. Pat. No. 6,165,992 and U.S. Pat. No. 6,720,162 (kinase assays); U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Kinase assays. In some preferred embodiments the screening assay detects the ability of the test agent to modulate the kinase activity of a PIK4CA polypeptide. In further embodiments, a cell-free kinase assay system is used to identify a candidate RAC modulating agent, and a secondary, cell-based assay, such as an apoptosis or hypoxic induction assay (described below), may be used to further characterize the candidate RAC modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Yet other assays for kinases involve uncoupled, pH sensitive assays that can be used for high-throughput screening of potential inhibitors or for determining substrate specificity. Since kinases catalyze the transfer of a gamma-phosphoryl group from ATP to an appropriate hydroxyl acceptor with the release of a proton, a pH sensitive assay is based on the detection of this proton using an appropriately matched buffer/indicator system (Chapman E and Wong C H (2002) Bioorg Med Chem. 10:551-5).

Apoptosis assays. Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™Homogeneous Caspase-3/7 assay from Promega, cat# 67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat# 1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumalation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses a PIK4CA, and that optionally has defective RAC function (e.g. RAC is over-expressed or under-expressed relative to wild-type cells). A test agent can be added to the apoptosis assay system and changes in induction of apoptosis relative to controls where no test agent is added, identify candidate RAC modulating agents. In some embodiments of the invention, an apoptosis assay may be used as a secondary assay to test a candidate RAC modulating agents that is initially identified using a cell-free assay system. An apoptosis assay may also be used to test whether PIK4CA function plays a direct role in apoptosis. For example, an apoptosis assay may be performed on cells that over- or under-express PIK4CA relative to wild type cells. Differences in apoptotic response compared to wild type cells suggests that the PIK4CA plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al, 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.# G5421).

Cell proliferation may also be assayed by colony formation in soft agar, or clonogenic survival assay (Sambrook et al., Molecular Cloning, Cold Spring Harbor (1989)). For example, cells transformed with PIK4CA are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a PIK4CA may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a PIK4CA, and that optionally has defective RAC function (e.g. RAC is over-expressed or under-expressed relative to wild-type cells). A test agent can be added to the assay system and changes in cell proliferation or cell cycle relative to controls where no test agent is added, identify candidate RAC modulating agents. In some embodiments of the invention, the cell proliferation or cell cycle assay may be used as a secondary assay to test a candidate RAC modulating agents that is initially identified using another assay system such as a cell-free assay system. A cell proliferation assay may also be used to test whether PIK4CA function plays a direct role in cell proliferation or cell cycle. For example, a cell proliferation or cell cycle assay may be performed on cells that over- or under-express PIK4CA relative to wild type cells. Differences in proliferation or cell cycle compared to wild type cells suggests that the PIK4CA plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a PIK4CA, and that optionally has defective RAC function (e.g. RAC is over-expressed or under-expressed relative to wild-type cells). A test agent can be added to the angiogenesis assay system and changes in angiogenesis relative to controls where no test agent is added, identify candidate RAC modulating agents. In some embodiments of the invention, the angiogenesis assay may be used as a secondary assay to test a candidate RAC modulating agents that is initially identified using another assay system. An angiogenesis assay may also be used to test whether PIK4CA function plays a direct role in cell proliferation. For example, an angiogenesis assay may be performed on cells that over- or under-express PIK4CA relative to wild type cells. Differences in angiogenesis compared to wild type cells suggests that the PIK4CA plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with PIK4CA in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a PIK4CA, and that optionally has defective RAC function (e.g. RAC is over-expressed or under-expressed relative to wild-type cells). A test agent can be added to the hypoxic induction assay system and changes in hypoxic response relative to controls where no test agent is added, identify candidate RAC modulating agents. In some embodiments of the invention, the hypoxic induction assay may be used as a secondary assay to test a candidate RAC modulating agents that is initially identified using another assay system. A hypoxic induction assay may also be used to test whether PIK4CA function plays a direct role in the hypoxic response. For example, a hypoxic induction assay may be performed on cells that over- or under-express PIK4CA relative to wild type cells. Differences in hypoxic response compared to wild type cells suggests that the PIK4CA plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the PIK4CA protein. Methods for testing antibody affinity and specificity are well known in the art (Harlow and Lane, 1988, 1999, supra). The enzyme-linked immunosorbant assay (ELISA) is a preferred method for detecting PIK4CA-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance PIK4CA gene expression, preferably mRNA expression. In general, expression analysis comprises comparing PIK4CA expression in like populations of cells (e.g., two pools of cells that endogenously or recombinantly express PIK4CA) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that PIK4CA mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the PIK4CA protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve PIK4CA mRNA expression, may also be used to test nucleic acid modulators.

Secondary Assays

Secondary assays may be used to further assess the activity of PIK4CA-modulating agent identified by any of the above methods to confirm that the modulating agent affects PIK4CA in a manner relevant to the RAC pathway. As used herein, PIK4CA-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with PIK4CA.

Secondary assays generally compare like populations of cells or animals (e.g., two pools of cells or animals that endogenously or recombinantly express PIK4CA) in the presence and absence of the candidate modulator. In general, such assays test whether treatment of cells or animals with a candidate PIK4CA-modulating agent results in changes in the RAC pathway in comparison to untreated (or mock- or placebo-treated) cells or animals. Certain assays use "sensitized genetic backgrounds", which, as used herein, describe cells or animals engineered for altered expression of genes in the RAC or interacting pathways.

Cell-Based Assays

Cell based assays may detect endogenous RAC pathway activity or may rely on recombinant expression of RAC pathway components. Any of the aforementioned assays may be used in this cell-based format. Candidate modulators are typically added to the cell media but may also be injected into cells or delivered by any other efficacious means.

Animal Assays

A variety of non-human animal models of normal or defective RAC pathway may be used to test candidate PIK4CA modulators. Models for defective RAC pathway typically use genetically modified animals that have been engineered to mis-express (e.g., over-express or lack expression in) genes involved in the RAC pathway. Assays generally require systemic delivery of the candidate modulators, such as by oral administration, injection, etc.

In a preferred embodiment, RAC pathway activity is assessed by monitoring neovascularization and angiogenesis. Animal models with defective and normal RAC are used to test the candidate modulator's affect on PIK4CA in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the PIK4CA. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on PIK4CA is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the PIK4CA endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorigenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific PIK4CA-modulating agents are useful in a variety of diagnostic and therapeutic applications where disease or disease prognosis is related to defects in the RAC pathway, such as angiogenic, apoptotic, or cell proliferation disorders. Accordingly, the invention also provides methods for modulating the RAC pathway in a cell, preferably a cell pre-determined to have defective or impaired RAC function (e.g. due to overexpression, underexpression, or misexpression of RAC, or due to gene mutations), comprising the step of administering an agent to the cell that specifically modulates PIK4CA activity. Preferably, the modulating agent produces a detectable phenotypic change in the cell indicating that the RAC function is restored. The phrase "function is restored", and equivalents, as used herein, means that the desired phenotype is achieved, or is brought closer to normal compared to untreated cells. For example, with restored RAC function, cell proliferation and/or progression through cell cycle may normalize, or be brought closer to normal relative to untreated cells. The invention also provides methods for treating disorders or disease associated with impaired RAC function by administering a therapeutically effective amount of a PIK4CA-modulating agent that modulates the RAC pathway. The invention further provides methods for modulating PIK4CA function in a cell, preferably a cell pre-determined to have defective or impaired PIK4CA function, by administering a PIK4CA-modulating agent. Additionally, the invention provides a method for treating disorders or disease associated with impaired PIK4CA function by administering a therapeutically effective amount of a PIK4CA-modulating agent.

The discovery that PIK4CA is implicated in RAC pathway provides for a variety of methods that can be employed for the diagnostic and prognostic evaluation of diseases and disorders involving defects in the RAC pathway and for the identification of subjects having a predisposition to such diseases and disorders.

Various expression analysis methods can be used to diagnose whether PIK4CA expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective RAC signaling that express a PIK4CA, are identified as amenable to treatment with a PIK4CA modulating agent. In a preferred application, the RAC defective tissue overexpresses a PIK4CA relative to normal tissue. For example, a Northern blot analysis of mRNA from tumor and normal cell lines, or from tumor and matching normal tissue samples from the same patient, using full or partial PIK4CA cDNA sequences as probes, can determine whether particular tumors express or overexpress PIK4CA. Alternatively, the TaqMan® is used for quantitative RT-PCR analysis of PIK4CA expression in cell lines, normal tissues and tumor samples (PE Applied Biosystems).

Various other diagnostic methods may be performed, for example, utilizing reagents such as the PIK4CA oligonucleotides, and antibodies directed against a PIK4CA, as described above for: (1) the detection of the presence of PIK4CA gene mutations, or the detection of either over- or under-expression of PIK4CA mRNA relative to the non-disorder state; (2) the detection of either an over- or an under-abundance of PIK4CA gene product relative to the non-disorder state; and (3) the detection of perturbations or abnormalities in the signal transduction pathway mediated by PIK4CA.

Kits for detecting expression of PIK4CA in various samples, comprising at least one antibody specific to PIK4CA, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in PIK4CA expression, the method comprising: a) obtaining a biological sample from the patient; b) contacting the sample with a probe for PIK4CA expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *C. elegans* RAC Enhancer Screen

A genetic screen was designed to identify modifiers of the Rac signaling pathway that also affect cell migrations in *C. elegans*. The basis of this screen is the observation that ced-10 and mig-2 single mutants resemble wildtype worms in morphology and movement, whereas double mutants have strong morphological and movement defects. In the primary screen, the function of individual genes is inactivated by RNA interference (RNAi) in wildtype, ced-10 and mig-2 worms at the L4 stage. The progeny of the RNA treated animals are then examined for morphological and movement defects resembling those of the ced-10; mig-2 double mutant. All genes that give such a phenotype in a ced-10 or mig-2 mutant background but not in a wildtype background are then tested in a direct cell migration assay. In the cell migration assay, a subset of mechanosensory neurons known as AVM and ALM are scored for their final positions in the animal using a GFP marker expressed in these cells. This migration assay is done in both wildtype and a ced-10 or mig-2 mutant background. Since the AVM and ALM cells normally migrate and reach their final position during the first larval stage, scoring of position is done in later larval or adult stages. Those genes that cause short or misguided migrations of these neurons when inactivated in a wildtype or rac mutant background are potentially relevant for treatment of diseases that involve cell migrations.

BLAST analysis (Altschul et al., supra) was employed to identify orthologs of *C. elegans* modifiers. For example, representative sequence from PIK4CA, GI# 17105400 (SEQ ID NO:8) shares 53% amino acid identity with the *C. elegans* 3N342.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10(11): 1679-89) programs. For example, the kinase domain (PFAM 00613) of PIK4CA from GI# 17105400 (SEQ ID NO:8) is located at approximately amino acid residues 1501 to 1670, and 1786 to 1993.

II. Kinase Assay

A purified or partially purified PIK4CA is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

III. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, U C Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| PIK4CA Seq ID | 1 |
|---|---|
| Breast | 21% |
| # of Pairs | 34 |
| Colon | 22% |
| # of Pairs | 40 |
| Head And Neck | 31% |
| # of Pairs | 13 |
| Kidney | 14% |
| # of Pairs | 21 |
| Liver | 22% |
| # of Pairs | 9 |
| Lung | 8% |
| # of Pairs | 40 |
| Lymphoma | 0% |
| # of Pairs | 4 |
| Ovary | 16% |
| # of Pairs | 19 |
| Pancreas | 67% |
| # of Pairs | 12 |
| Prostate | 8% |
| # of Pairs | 24 |
| Skin | 29% |
| # of Pairs | 7 |
| Stomach | 9% |
| # of Pairs | 11 |
| Testis | 0% |
| # of Pairs | 8 |
| Thyroid Gland | 7% |
| # of Pairs | 14 |
| Uterus | 4% |
| # of Pairs | 23 |

IV. PIK4CA Functional Assays

RNAi experiments were carried out to knock down expression of PIK4CA (SEQ ID NO: 1) in various cell lines using small interfering RNAs (siRNA, Elbashir et al, supra).

Effect of PIK4CA RNAi on apoptosis. The Phospho-histone H2B assay, as described above, was employed to study the effects of decreased PIK4CA expression on apoptosis. The results of this experiment indicated that RNAi of PIK4CA increased apoptosis in A549 lung cancer cells, SW480 colon cancer cells, and U87MG glioblastoma cells.

Multiple parameter apoptosis assay, as described above, was also used to study the effects of decreased PIK4CA expression on apoptosis. The results of this experiment indicated that RNAi of PIK4CA increased apoptosis in A549 lung cancer cells, SW480 colon cancer cells, and U87MG glioblastoma cells, using caspase 3 and also phospho-histone H2B as readouts.

What is claimed is:

1. A method of identifying a candidate RAC pathway inhibitory agent, said method comprising the steps of:
   (a) providing an assay system comprising a phosphatidylinositol 4-kinase (PIK4CA) nucleic acid, wherein the assay system is capable of detecting the expression of PIK4CA nucleic acid;
   (b) contacting the assay system with a candidate test agent; and
   (c) determining the expression of PIK4CA nucleic acid in the assay system, wherein a decrease in PIK4CA nucleic acid expression between the presence and absence of said candidate test agent identifies the test agent as a candidate RAC pathway inhibitory agent.

2. The method of claim 1, wherein the assay system comprises cultured cells that express the PIK4CA polypeptide.

3. The method of claim 2, wherein the cultured cells additionally have defective RAC function.

4. The method of claim 1, wherein the assay system is selected from the group consisting of an apoptosis assay system, a cell proliferation assay system, an angiogenesis assay system, and a hypoxic induction assay system.

5. The method of claim 1, wherein the assay system includes an expression assay comprising a PIK4CA nucleic acid and the candidate test agent is a nucleic acid modulator.

6. The method of claim 5, wherein the nucleic acid modulator is an antisense oligomer.

7. The method of claim 5, wherein the nucleic acid modulator is a phosphorodiamidate morpholino oligomer (PMO).

8. The method of claim 5, wherein the nucleic acid modulator is an siRNA.

* * * * *